(12) United States Patent
Fadli et al.

(10) Patent No.: US 10,240,043 B2
(45) Date of Patent: Mar. 26, 2019

(54) USE FOR DYEING KERATIN FIBRES OF A COMPOUND OF AZOMETHINE TYPE BEARING TWO PYRAZOLOPYRIDINE UNITS

(71) Applicant: L'OREAL, Paris (FR)

(72) Inventors: Aziz Fadli, Chelles (FR); Stephane Blais, Palaiseau (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/536,747

(22) PCT Filed: Dec. 17, 2015

(86) PCT No.: PCT/EP2015/080323
§ 371 (c)(1),
(2) Date: Jun. 16, 2017

(87) PCT Pub. No.: WO2016/097198
PCT Pub. Date: Jun. 23, 2016

(65) Prior Publication Data
US 2017/0349753 A1   Dec. 7, 2017

(30) Foreign Application Priority Data
Dec. 19, 2014 (FR) ...................................... 14 63006

(51) Int. Cl.
| | |
|---|---|
| *A61Q 5/10* | (2006.01) |
| *C09B 55/00* | (2006.01) |
| *A61Q 5/06* | (2006.01) |
| *C07D 471/04* | (2006.01) |
| *C09B 69/10* | (2006.01) |
| *A61K 8/49* | (2006.01) |

(52) U.S. Cl.
CPC ............ *C09B 55/006* (2013.01); *A61K 8/494* (2013.01); *A61Q 5/065* (2013.01); *A61Q 5/10* (2013.01); *C07D 471/04* (2013.01); *C09B 69/107* (2013.01)

(58) Field of Classification Search
CPC ...... A61Q 5/065; A61K 8/494; C07D 471/04; C09B 69/07; C09B 55/006
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 5,792,221 A | 8/1998 | Lagrange et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,884,265 B2 | 4/2005 | Vidal et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

STIC Search Report dated Jul. 3, 2018.*
International Search Report for PCT/EP2015/080323, dated Feb. 23, 2016.

*Primary Examiner* — Eisa B Elhilo
(74) *Attorney, Agent, or Firm* — The Marbury Law Group, PLLC

(57) ABSTRACT

The invention relates to a compound chosen from the compounds of formulae (I) and (II), the leucoforms thereof, the optical and geometrical isomers thereof and the tautomers thereof, and also the addition salts thereof with an acid or a base, and the solvates thereof. The invention also relates to the use of these particular compounds for dyeing keratin fibres.

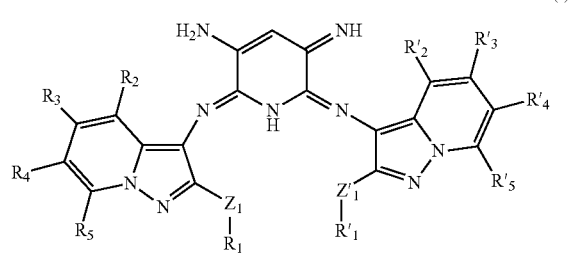

(I)

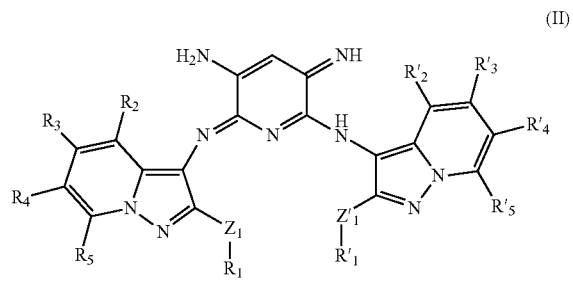

(II)

14 Claims, No Drawings

(56) References Cited

U.S. PATENT DOCUMENTS

| | | |
|---|---|---|
| 7,060,110 B2 | 6/2006 | Vidal et al. |
| 7,582,123 B2 | 9/2009 | Fadli et al. |
| 7,892,294 B2 * | 2/2011 | Fadli ............... A61K 8/494 132/202 |
| 2002/0095732 A1 | 7/2002 | Kravtchenko et al. |
| 2003/0106169 A1 | 6/2003 | Vidal et al. |
| 2004/0093675 A1 | 5/2004 | Vidal et al. |
| 2004/0093676 A1 | 5/2004 | Vidal et al. |
| 2004/0107513 A1 | 6/2004 | Vidal et al. |
| 2004/0127692 A1 | 7/2004 | David et al. |
| 2004/0143911 A1 | 7/2004 | Vidal |
| 2004/0168263 A1 | 9/2004 | Vidal |
| 2004/0200009 A1 | 10/2004 | Vidal |
| 2004/0244123 A1 | 12/2004 | Vidal et al. |
| 2005/0039268 A1 | 2/2005 | Plos et al. |
| 2005/0060815 A1 | 3/2005 | Kravtchenko et al. |
| 2006/0053568 A1 | 3/2006 | Fadli |
| 2007/0136959 A1 | 6/2007 | Fadli |
| 2007/0143935 A1 | 6/2007 | Fadli |
| 2009/0044348 A1 | 2/2009 | Fadli |
| 2010/0115711 A1 | 5/2010 | Fadli et al. |

FOREIGN PATENT DOCUMENTS

| | | |
|---|---|---|
| DE | 1133957 A1 | 4/1993 |
| DE | 19543988 A1 | 5/1997 |
| EP | 0714954 A2 | 6/1996 |
| EP | 0770375 A1 | 5/1997 |
| EP | 1634574 A2 | 3/2006 |
| EP | 1792606 A1 | 6/2007 |
| EP | 1792903 A1 | 6/2007 |
| EP | 2011787 A1 | 1/2009 |
| FR | 2692572 A1 | 12/1993 |
| FR | 2733749 A1 | 11/1996 |
| FR | 2750048 A1 | 12/1997 |
| FR | 2807650 A1 | 10/2001 |
| FR | 2822693 A1 | 10/2002 |
| FR | 2822694 A1 | 10/2002 |
| FR | 2822696 A1 | 10/2002 |
| FR | 2822698 A1 | 10/2002 |
| FR | 2825625 A1 | 12/2002 |
| FR | 2825702 A1 | 12/2002 |
| FR | 2829926 A1 | 3/2003 |
| FR | 2844269 A1 | 3/2004 |
| FR | 2892924 A1 | 5/2007 |
| FR | 2917737 A1 | 12/2008 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A | 6/1995 |
| WO | 96/15765 A1 | 5/1996 |
| WO | 02/078660 A1 | 10/2002 |
| WO | 02/100369 A1 | 12/2002 |
| WO | 02/100834 A1 | 12/2002 |
| WO | 2004/031173 A1 | 4/2004 |

* cited by examiner

USE FOR DYEING KERATIN FIBRES OF A COMPOUND OF AZOMETHINE TYPE BEARING TWO PYRAZOLOPYRIDINE UNITS

CROSS REFERENCE TO RELATED APPLICATIONS

This is a national stage application of PCT/EP2015/080323, filed internationally on Dec. 17, 2015, which claims priority to French Application No. 1463006, filed on Dec. 19, 2014, both of which are incorporated by reference herein in their entireties.

The present invention relates to novel compounds of azomethine type bearing two pyrazolopyridine units and to the use thereof for dyeing keratin fibres, and in particular human keratin fibres such as the hair.

It is known practice to dye keratin fibres with dye compositions containing direct dyes. These compounds are coloured and colouring molecules that have affinity for the fibres. It is known practice, for example, to use direct dyes of the nitrobenzene type, anthraquinone or nitropyridine dyes, and dyes of the azo, xanthene, acridine, azine or triarylmethane type.

These dyes are usually applied to fibres optionally in the presence of an oxidizing agent if it is desired to obtain simultaneous lightening of the fibres. Once the leave-on time has elapsed, the fibres are rinsed, optionally washed and dried.

The colourings resulting from the use of direct dyes are colourings that are often chromatic but are, however, only temporary or semi-permanent since the nature of the interactions that bind the direct dyes to the keratin fibre and their desorption from the surface and/or the core of the fibre are responsible for their weak dyeing power and their poor relative persistence with respect to washing or perspiration. These direct dyes are also generally light-sensitive since the resistance of the chromophore to photochemical attack is low, leading to fading of the colouring of the hair over time. The sensitivity of these dyes to light depends on their uniform distribution or their distribution as aggregates in and/or on the keratin fibre.

To obtain the same result, it is also possible to use the uncoloured reduced form of these dyes and to apply it to the keratin fibres in the presence of an oxidizing agent in order to generate the coloured and colouring oxidized form. The colouring obtained may then be faded out and then reformed rapidly by changing from one form to the other.

Thus, it is known from French patent application No. 2 917 737 to use compounds of azomethine type bearing a pyrazolinone unit and the reduced forms thereof to obtain a colouring on keratin fibres that can be faded out and then reformed readily.

The aim of the present invention is to provide novel direct dyes for reversibly dyeing keratin fibres while at the same time leading to good dyeing properties.

In particular, one of the aims of the present invention is to provide direct dyes that make it possible to obtain a strong, chromatic, aesthetic, sparingly selective colouring with varied shades, which shows good resistance to the various attacking factors to which the hair may be subjected such as shampoos, light, sweat and permanent reshaping, and which can be faded out easily.

The Applicant has thus discovered, surprisingly, that particular compounds chosen from dyes of azomethine type comprising two pyrazolopyridine units of formulae (I) and (II) as defined below, the leuco forms thereof and also the optical and geometrical isomers and tautomers thereof, the addition salts thereof with an acid or a base and the solvates thereof such as hydrates make it possible to achieve this aim.

One subject of the invention is thus a compound chosen from the dyes of formulae (I) and (II) below, and also the leuco forms thereof, the optical isomers and geometrical isomers thereof, the tautomers thereof, the addition salts thereof with an acid or a base, and the solvates thereof such as hydrates:

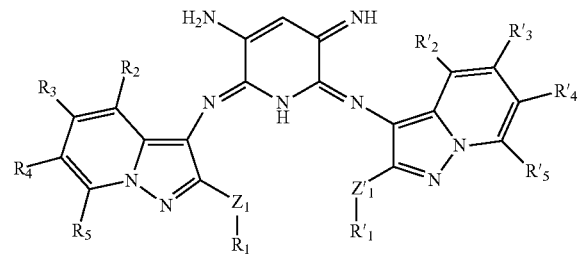

(I)

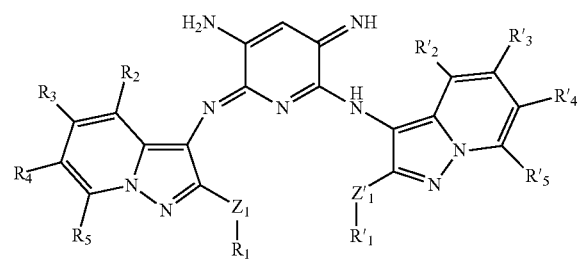

(II)

in which formulae (I) and (II):
$Z_1$ represents an oxygen atom or a group —N($R_6$)—;
$Z'_1$ represents an oxygen atom or a group —N($R'_6$)—;
when $Z_1$ represents —N($R_6$)— and/or $Z'_1$ represents —N($R'_6$)— then $R_1$ and $R_6$ and/or $R'_1$ and $R'_6$, respectively, may form, together with the nitrogen atom to which they are attached, an optionally substituted, 5- to 8-membered, optionally cationic, saturated, unsaturated or aromatic heterocycle;
$R_1$, $R'_1$, $R_6$, and $R'_6$ each independently represent:
  a hydrogen atom;
  a $C_1$-$C_{10}$ alkyl radical optionally interrupted with one or more non-adjacent heteroatoms, preferably oxygen, and/or optionally substituted, preferably with one or more groups chosen from i) hydroxyl, ii) optionally substituted, 5- to 8-membered, cationic or non-cationic, saturated, unsaturated or aromatic (hetero)cycle, iii) —N(R')R", iv) —N⁺R'R"R''' with R', R" and R''' each independently representing a $C_1$-$C_6$ alkyl group;
  an optionally substituted, 5- to 8-membered, cationic or non-cationic, saturated, unsaturated or aromatic (hetero)cyclic radical;
  in particular, $R_1$ and $R'_1$, which may be identical or different, preferably identical, represent a (poly)hydroxy($C_1$-$C_6$ alkyl), preferably hydroxy($C_1$-$C_6$ alkyl) and $Z_1$ and $Z'_1$ represent an oxygen atom;
$R_2$, $R_3$, $R_4$, $R_5$, $R'_2$, $R'_3$, $R'_4$ and $R'_5$ each independently represent:
  a hydrogen atom,
  an optionally substituted $C_1$-$C_4$ alkyl radical, a group chosen from —NH$_2$, —N(H)R$_{10}$, —N(R$_{11}$)R$_{12}$, OH and —OR$_9$, with R$_9$ and R$_{10}$ representing an optionally substituted, linear or branched C$_1$-C$_6$ alkyl, R$_{11}$ and R$_{12}$, which may be identical or different, representing an optionally substituted, linear or branched C$_1$-C$_6$ alkyl, it being possible for R$_{11}$ and R$_{12}$ to form, together with the nitrogen atom to which they are attached, a saturated, unsaturated or aromatic 5- to 8-membered heterocycle optionally containing one or more other heteroatoms or groups chosen from N, O, S, S(O)$_2$ and C(O), the heterocycle being optionally substituted;

R$_2$, R$_3$, R$_4$, R$_5$, R'$_2$, R'$_3$, R'$_4$ and R'$_5$ may form, in pairs with adjacent radicals, an optionally substituted, saturated or unsaturated (hetero)cycle;

it being understood that when the compound of formula (I) or (II) is positively charged, then it comprises as many anionic counterions as cationic charges to achieve the electrical neutrality of the molecule.

The compounds according to the invention, as defined above, are useful for dyeing keratin fibres. They make it possible to obtain a strong, chromatic, aesthetic, sparingly selective colouring in varied shades, which can be faded out easily and/or which can be recoloured easily after fading out. In addition, the colourings obtained using dye (I) or (II) successfully withstand the various attacking factors to which hair may be subjected, such as shampooing, light, sweat and permanent reshaping.

A subject of the present invention is also the use of at least one of these compounds chosen from the compounds of formulae (I) and (II) as defined in the present invention, the leuco forms, optical isomers, geometrical isomers and tautomers thereof, and also the addition salts with an acid or a base and the solvates thereof, for dyeing keratin fibres, in particular human keratin fibres such as the hair.

More particularly, they lead to intense colourings at different pH values, better still at neutral and basic pH, and even more preferentially at neutral pH.

Another subject of the invention is a composition for dyeing keratin fibres, comprising, in a medium that is suitable for dyeing, at least one compound according to the invention.

A subject of the present invention is also a process for dyeing keratin fibres using compounds according to the invention.

A subject of the present invention is also a multi-compartment device or kit for performing the process in accordance with the invention.

Other subjects, characteristics, aspects and advantages of the invention will emerge even more clearly on reading the description and the examples that follow.

In the text hereinbelow, unless otherwise indicated, the limits of a range of values are included in that range, especially in the expressions "between" and "ranging from . . . to . . . ".

The expression "at least one" used in the present description is equivalent to the expression "one or more".

In the context of the invention, unless otherwise mentioned, the term "alkyl radical" means linear or branched alkyl radicals.

The saturated or unsaturated and optionally fused rings can also be optionally substituted.

The alkyl radicals are saturated, linear or branched hydrocarbon-based radicals, generally of C$_1$-C$_{10}$, preferably C$_1$-C$_6$ alkyl radicals, such as methyl, ethyl, propyl, butyl, pentyl and hexyl.

The alkenyl radicals are unsaturated, linear or branched C$_2$-C$_{10}$ hydrocarbon-based radicals, comprising at least one double bond, particularly C$_2$-C$_6$ alkenyl radicals such as ethylene, propylene, butylene, pentylene, 2-methylpropylene and decylene.

The alkynyl radicals are unsaturated, linear or branched C$_2$-C$_{10}$ hydrocarbon-based radicals, comprising at least one triple bond, particularly C$_2$-C$_6$ alkynyl radicals.

The alkoxy radicals are alkyl-oxy radicals with alkyl as defined above, preferably C$_1$-C$_{10}$ alkyl, such as methoxy, ethoxy, propoxy and butoxy.

The alkoxyalkyl radicals are preferably (C$_1$-C$_{20}$)alkoxy(C$_1$-C$_{20}$)alkyl radicals, such as methoxymethyl, ethoxymethyl, methoxyethyl and ethoxyethyl.

For the purposes of the present invention, the term "interrupted" means that the alkyl group is interrupted on the carbon-based chain of said alkyl with one or more heteroatoms. Examples that may be mentioned include -Ak-O-Ak", -Ak-N(R)-Ak", -Ak-O-Ak'-N(R)-Ak", -Ak-N(R)-Ak'-N(R)-Ak" or -Ak-O-Ak'-O-Ak", with Ak and Ak' representing C$_1$-C$_4$ alkylene groups and Ak" representing a C$_1$-C$_4$ alkyl group.

The halogens are preferably chosen from fluorine, chlorine, bromine and iodine atoms.

The "alkylcarbonyl" radicals are alkyl-carbonyl radicals with alkyl as defined previously, preferably C$_1$-C$_{10}$ alkyl, such as acetyl or propionyl.

The "alkoxycarbonyl" radicals are —O—C(O)-alkyl radicals with alkyl as defined previously, for instance acetate, propionate, citrate, tartrate, gluconate and lactate.

The "alkyl", "alkenyl", "cyclic" or "cycloalkyl" radicals, when they are substituted, are substituted with at least one substituent borne by at least one carbon atom chosen from: 1) a halogen atom, a group chosen from 2) hydroxyl; 3) oxo; 4) C$_1$-C$_2$ alkoxy; 5) C$_1$-C$_{10}$ alkoxycarbonyl; 6) C$_1$-C$_{10}$ alkylcarbonyl; 7) (poly)hydroxy(C$_2$-C$_4$)alkyl; 8) (poly)hydroxy(C$_2$-C$_4$)alkoxy; 9) amino; 10) quaternary ammonium —N$^+$R'R"R'", M$^-$ for which R', R" and R'", which may be identical or different, represent a hydrogen atom, or a C$_1$-C$_4$ alkyl group; and M$^-$ represents an anionic counterion, in particular a halide; 11) 5- or 6-membered heterocycloalkyl; 12) optionally cationic 5- or 6-membered heteroaryl, preferentially imidazolium, optionally substituted with a C$_1$-C$_4$ alkyl radical, preferentially methyl; 13) amino substituted with one or two identical or different C$_1$-C$_6$ alkyl radicals optionally bearing at least: i) a hydroxyl group, ii) amino optionally substituted with one or two C$_1$-C$_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —N$^+$R'R"R'", M$^-$ for which R', R" and R'", which may be identical or different, represent a hydrogen atom, or a C$_1$-C$_4$ alkyl group; and M$^-$ represents an anionic counterion, in particular a halide; iv) optionally cationic 5- or 6-membered heteroaryl, preferentially imidazolium, optionally substituted with a C$_1$-C$_4$ alkyl radical, preferentially methyl; 14) acylamino (—NR—C(O)—R') in which the radical R is a hydrogen atom or a C$_1$-C$_4$ alkyl radical optionally bearing at least one hydroxyl group and the radical R' is a C$_1$-C$_2$ alkyl radical; 15) carbamoyl ((R)$_2$N—C(O)—) in which the radicals R, which may be identical or different, represent a hydrogen atom or a C$_1$-C$_4$ alkyl radical optionally bearing at least one hydroxyl group; 16) alkylsulfonylamino (R'—S(O)$_2$—N(R)—) in which the radical R represents a hydrogen atom or a C$_1$-C$_4$ alkyl radical optionally bearing at least one hydroxyl group and the radical R' represents a $C_1$-$C_4$ alkyl radical, a phenyl radical; 17) aminosulfonyl $((R)_2N—S(O)_2—)$ in which the radicals R, which may be identical or different, represent a hydrogen atom or a $C_1$-$C_4$ alkyl radical optionally bearing at least one hydroxyl group; 18) carboxyl in acid or salified form (preferably salified with an alkali metal or a substituted or unsubstituted ammonium); 19) cyano; 20) nitro; 21) nitroso; 22) phenoxy optionally substituted with one or more hydroxyl groups; 23) phenylcarbonyloxy optionally substituted with one or more hydroxyl groups; 24) phenyloxycarbonyl optionally substituted with one or more hydroxyl groups; and 25) a phenyl group optionally substituted with one or more hydroxyl groups.

The "aryl", "heterocyclic" or "heteroaryl" radicals or the aryl, heteroaryl or heterocyclic part of the radicals, when they are substituted, are substituted with at least one substituent borne by at least one carbon atom, chosen from: 1) halogen; 2) $C_1$-$C_{10}$ alkyl, preferably $C_1$-$C_8$ alkyl, optionally substituted with one or more radicals chosen from the following radicals: i) hydroxyl, ii) $C_1$-$C_2$ alkoxy, iii) (poly)hydroxy($C_2$-$C_4$)alkoxy, iv) acylamino, v) amino substituted with two identical or different $C_1$-$C_4$ alkyl radicals optionally bearing at least one hydroxyl group or it being possible for the two radicals to form, with the nitrogen atom to which they are attached, a saturated or unsaturated 5- to 7-membered, preferably 5- or 6-membered, heterocycle optionally comprising another nitrogen or non-nitrogen heteroatom; 3) hydroxyl; 4) $C_1$-$C_2$ alkoxy; 5) $C_1$-$C_{10}$ alkoxycarbonyl; 6) $C_1$-$C_{10}$ alkylcarbonyloxy; 7) (poly)hydroxy($C_2$-$C_4$)alkoxy; 8) amino; 9) 5- or 6-membered heterocycloalkyl; 10) optionally cationic 5- or 6-membered heteroaryl, preferentially imidazolium, optionally substituted with a $(C_1$-$C_4)$alkyl radical, preferentially methyl; 11) amino substituted with one or two identical or different $C_1$-$C_6$ alkyl radicals optionally bearing at least: i) hydroxyl, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium $—N^+R'R''R'''$, $M^-$ for which R', R" and R''', which may be identical or different, represent a hydrogen atom or a $C_1$-$C_4$ alkyl group; and $M^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 12) quaternary ammonium $—N^+R'R''R'''$, $M^-$ for which R', R", R''' and $M^-$ are as defined previously; 13) acylamino $(—N(R)—C(O)—R')$ in which the radical R is a hydrogen atom or a $C_1$-$C_4$ alkyl radical optionally bearing at least one hydroxyl group and the radical R' is a $C_1$-$C_2$ alkyl radical; 14) carbamoyl $((R)_2N—C(O)—)$ in which the radicals R, which may be identical or different, represent a hydrogen atom or a $C_1$-$C_4$ alkyl radical optionally bearing at least one hydroxyl group; 15) alkylsulfonylamino $(R'S(O)_2—N(R)—)$ in which the radical R represents a hydrogen atom or a $C_1$-$C_4$ alkyl radical optionally bearing at least one hydroxyl group and the radical R' represents a $C_1$-$C_4$ alkyl radical, a phenyl radical; 16) aminosulfonyl $((R)_2N—S(O)_2—)$ in which the radicals R, which may be identical or different, represent a hydrogen atom or a $C_1$-$C_4$ alkyl radical optionally bearing at least one hydroxyl group; 17) carboxyl in acid or salified form (preferably salified with an alkali metal or a substituted or unsubstituted ammonium); 18) cyano; 19) nitro; 20) nitroso; 21) polyhaloalkyl, preferentially trifluoromethyl; 22) carboxyl; 23) phenylcarbonyloxy optionally substituted with one or more hydroxyl groups; 24) phenyloxycarbonyl optionally substituted with one or more hydroxyl groups; 25) phenyl optionally substituted with one or more hydroxyl or alkoxy groups; and 26) phenoxy.

The term "optionally substituted amino" means an amino group which may bear one or two 1) identical or different $C_1$-$C_6$ alkyl radicals optionally bearing at least: i) a hydroxyl group, ii) an amino group optionally substituted with one or two $C_1$-$C_3$ alkyl radicals, said alkyl radicals or the two alkyl radicals form, with the nitrogen atom to which they are attached, a saturated or unsaturated, optionally substituted 5- to 7-membered heterocycle optionally comprising at least one other nitrogen or non-nitrogen heteroatom; 2) —C(O)(alkyl), the alkyl group possibly being substituted; 3) —C(O)O(alkyl), the alkyl group possibly being substituted; 4) —C(O)NH(alkyl), the alkyl group possibly being substituted; 5) —SO$_2$(alkyl), the alkyl group possibly being substituted.

The "cyclic" radicals are fused or non-fused, saturated or unsaturated, aromatic or non-aromatic, monocyclic or polycyclic radicals, comprising from 4 to 30 carbon ring members, preferentially from 5 to 15 carbon atoms, optionally substituted with one or more atoms or groups as defined previously, especially one or more alkyl, alkoxy, carboxyl, hydroxyl, amine or oxo groups.

The "aryl" radicals are fused or non-fused, monocyclic or polycyclic carbon-based radicals, preferentially comprising from 6 to 20 carbon atoms, and of which at least one ring is aromatic; preferentially chosen from phenyl, biphenyl, naphthyl, indenyl, anthracenyl and tetrahydronaphthyl radicals; more preferentially, the aryl radicals of the invention are phenyl radicals.

The "heterocyclic" radicals are fused or non-fused, saturated or unsaturated, aromatic or non-aromatic, monocyclic or polycyclic, optionally cationic, 4- to 30-membered, preferentially 5- to 15-membered radicals, in at least one ring at least one ring member is a heteroatom, chosen in particular from O, N and S, preferably comprising from 1 to 6 heteroatoms, in particular 0 or N, optionally substituted with one or more atoms or groups as defined previously, especially one or more alkyl, alkoxy, carboxyl, hydroxyl, amine or oxo groups.

When the heterocycle is cationic, then it bears a cationic charge inside the ring (endocyclic) or outside the ring (exocyclic), i.e. the heterocycle is substituted with a cationic group.

The "heteroaryl" radicals are fused or non-fused, preferentially 5- to 22-membered monocyclic or polycyclic radicals, comprising from 1 to 6 heteroatoms chosen from nitrogen, oxygen and sulfur atoms, and at least one ring of which is aromatic; preferentially, the heteroaryl radicals are chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salts thereof.

Among the heterocyclic radicals that may be used in the invention, mention may be made more particularly of furyl, pyranyl, pyrrolyl, piperazinyl, piperidyl, morpholinyl, imidazolyl, pyrazolyl, pyridyl and thienyl groups. Preferably, the heterocyclic groups are fused heteroaryl groups such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, these groups possibly being substituted, in particular with one or more non-adjacent hydroxyl groups.

The "heterocycloalkyl" radicals are saturated heterocyclic radicals as defined previously, such as tetrahydrofuryl, tetrahydropyranyl, piperazinyl, piperidyl or morpholinyl.

The cycloalkyl radicals are cyclic radicals as defined previously, preferably saturated $C_4$-$C_8$ monocyclic radicals, such as cyclobutyl, cyclopentyl or cyclohexyl. The cycloalkyl radicals may be substituted, in particular with alkyl, alkoxy, carboxylic acid, hydroxyl, amine and ketone groups.

The nitrogenous heterocycle(s) formed by $R_1$ and $R_6$, and/or $R'_1$ and $R'_6$ may contain one or more other heteroatoms, especially a heteroatom chosen from N, O and S, one or more groups such as —S(O)—, —S(O)$_2$— and —C(O)—, and combinations thereof, and more particularly O or N. They may moreover be optionally substituted, especially as described above.

The term "anionic counterion" means an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$-OH O=P(O$^-$)$_3$, HO—[P(O)(O)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or SO$_4^{2-}$ and monosulfate HSO$_4^-$.

The anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a disulfide dye of formula (I) which contains two cationic chromophores may contain either two "singly charged" anionic counterions or a "doubly charged" anionic counterion such as (O=)$_2$S(O$^-$)$_2$ or O=P(O$^-$)$_2$—OH.

In formulae (I) and (II) above, when $R_1$, $R'_1$, $R_6$ and/or $R'_6$ represent a substituted alkyl radical, then the substituents are especially chosen from halogen atoms, —OH, —OR$_9$, —NH$_2$, —N(H)R$_{10}$ or —N(R$_{11}$)R$_{12}$ radicals, saturated or unsaturated cyclic radicals optionally containing a heteroatom chosen from N, S and O, the ring itself possibly being substituted, in which $R_9$, $R_{10}$, $R_{11}$ and $R_{12}$, which may be identical or different, represent a saturated linear or branched $C_1$-$C_6$ and preferably $C_1$-$C_4$ alkyl radical, such as methyl or ethyl. Preferably, mention may be made of —OH, —OR$_9$, —NH$_2$, —N(H)R$_{10}$ or —N(R$_{11}$)R$_{12}$ radicals and cyclic radicals such as imidazole, piperazine, pyrrolidine, pyridine, piperidine, morpholine and pyrimidine.

According to a particular embodiment of the invention, the compounds of formula (I) or (II) above are such that $Z_1$ and $Z'_1$, which may be identical or different, represent an oxygen atom, a radical —N(R$_6$)— and a radical —N(R'$_6$)- forming with $R_1$ and $R'_1$, respectively, a cationic or non-cationic heterocycle, such as piperazinyl, piperazinium, imidazolyl, pyrrolidinyl, pyridyl, morpholinyl, morpholinium, piperidyl or piperidinium, preferentially piperazinyl or piperazinium optionally substituted especially with one or more $C_1$-$C_4$ alkyl groups such as methyl.

The radicals $R_6$ and $R'_6$ may be chosen from a hydrogen atom; a $C_1$-$C_6$ alkyl radical and a $C_1$-$C_6$ alkyl radical substituted with one or more hydroxyl groups. According to this embodiment, $Z_1$ and $Z'_1$ preferably represent an oxygen atom or an NH radical.

According to the invention, the radicals $R_1$ and $R'_1$ may be chosen from the following groups: i) $C_1$-$C_6$ alkyl; ii) $C_1$-$C_{10}$ alkyl substituted with one or more hydroxyl groups; iii) $C_1$-$C_6$ alkyl substituted with one or more amino or (di)($C_1$-$C_4$) alkylamino groups such as dimethylamino; iv) $C_1$-$C_6$ alkyl substituted with a nitrogenous heterocycle, for example piperazinyl, imidazolyl, pyrrolidinyl, morpholinyl or piperidyl; v) —[(CH$_2$)$_m$—O]$_p$-L-Y with p=1, 2 or 3, preferably 1 or 2, m=1, 2 or 3, preferably 2, L denoting a linear or branched, saturated $C_1$-$C_6$ divalent hydrocarbon-based group, and Y denoting a hydroxyl group or a hydrogen atom.

Preferably, the radicals $R_1$ and $R'_1$ represent a $C_1$-$C_6$ alkyl group such as a methyl, ethyl, n-propyl, isopropyl or tert-butyl radical; a $C_1$-$C_6$ alkyl radical substituted with a hydroxyl group such as a hydroxyethyl or hydroxypropyl radical; a $C_1$-$C_6$ alkyl radical substituted with a di($C_1$-$C_4$) alkylamino such as a dimethylaminoethyl or dimethylaminopropyl radical; a $C_1$-$C_6$ alkyl radical substituted with a nitrogenous heterocycle chosen from imidazolyl, pyrrolidinyl, piperidyl, morpholinyl and piperazinyl, these heterocycles possibly being substituted; or a radical —[(CH$_2$)$_m$—O]$_p$-L-Y with m=2, p=1 or 2, L denoting an ethylene or isopropylene radical, and Y denoting a hydroxyl radical or a hydrogen atom.

According to the particular embodiment in which $Z_1$ and $Z'_1$ denote, respectively, a radical —NR$_6$ and —NR'$_6$ with $R_1$ and $R_6$ and $R'_1$ and $R'_6$ together forming a heterocycle with the nitrogen atom to which they are attached, the heterocycle is preferentially chosen from imidazolyl, piperazino, pyrrolidino, piperidino and morpholino, these heterocycles possibly being substituted, in particular with one or more $C_1$-$C_4$ alkyl or hydroxyl radicals.

According to a particular embodiment of the invention, the compounds of formulae (I) and (II) are such that $R_2$, $R'_2$, $R_3$, $R'_3$, $R_4$, $R'_4$, $R_5$ and $R'_5$ independently represent a hydrogen atom or a $C_1$-$C_4$ alkyl radical such as methyl, ethyl, propyl, isopropyl, butyl or tert-butyl, or $R_4$ and $R_5$ and $R'_4$ and $R'_5$ together form a 5- to 8-membered ring. Preferably, $R_2$, $R'_2$, $R_3$, $R'_3$, $R_4$, $R'_4$, $R_5$ and $R'_5$ independently represent a hydrogen atom or a $C_1$-$C_4$ alkyl radical such as methyl, ethyl, propyl, isopropyl, butyl or tert-butyl.

In the context of the invention, the term "derivative of formula (I) and/or (II)" means all mesomeric, tautomeric or optical or geometrical isomer forms, or leuco forms.

The term "addition salts" means the salts of physiologically acceptable organic or mineral acids of the compounds of formula (I) and/or (II).

The compounds of formulae (I) and/or (II) may be optionally salified with strong mineral acids, for instance HCl, HBr, HI, H$_2$SO$_4$ or H$_3$PO$_4$, or organic acids, for instance acetic acid, lactic acid, tartaric acid, citric acid, succinic acid, benzenesulfonic acid, para-toluenesulfonic acid, formic acid or methanesulfonic acid.

Moreover, the addition salts that may be used in the context of the invention are also chosen from addition salts with a cosmetically acceptable base such as the basifying agents as defined below, for instance alkali metal hydroxides such as sodium hydroxide, potassium hydroxide, aqueous ammonia, amines or alkanolamines.

The compounds of formula (I) or (II) may also be in the form of solvates, for example a hydrate or a solvate of a linear or branched alcohol such as ethanol or isopropanol.

The present invention makes it possible in particular to rapidly obtain chromatic colourings that withstand the various attacking factors to which hair may be subjected, in particular shampoos and light, which can be faded out and then reformed just as quickly.

The compounds of formula (I) and/or (II) are coloured and colouring species.

The compounds of formulae (I) and (II) are preferably symmetrical, i.e. $R_1$ represents the same radical as $R'_1$, which is likewise the case for $R_2$ and $R'_2$, $R_3$ and $R'_3$, $R_4$ and $R'_4$, $R_5$ and $R'_5$, $R_6$ and $R'_6$, and $Z_1$ and $Z'_1$.

According to another particular embodiment of the invention, the compounds of formulae (I) and (II) are non-cationic.

According to a particular embodiment, the azomethine dyes bearing two pyrazolopyridine units are chosen from the symmetrical compounds of formula (I') or (II') below, and also the leuco forms, optical isomers, geometrical isomers and tautomers thereof, the addition salts thereof with an acid or a base and the solvates thereof such as hydrates:

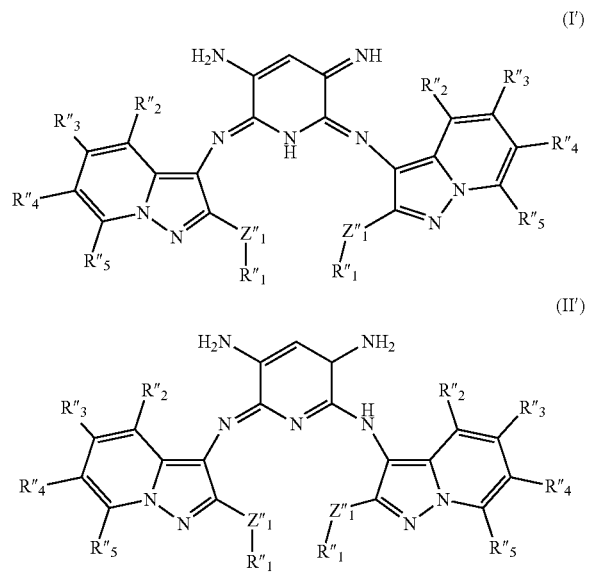

in which formulae (I') and (II'):

$Z''_1$ is chosen from an oxygen atom and a group —N(R''$_6$)—;

when $Z''_1$ represents —N(R''$_6$)—, then R''$_1$ and R''$_6$ may form, together with the nitrogen atom to which they are attached, an optionally substituted, 5- or 6-membered, saturated, unsaturated or aromatic heterocycle;

R''$_1$ represents a $C_1$-$C_6$ alkyl radical, optionally interrupted with one or more non-adjacent oxygen atoms, and/or optionally substituted with:

a hydroxyl radical, a di($C_1$-$C_4$)alkylamino radical, a heterocycle optionally substituted with one or more $C_1$-$C_4$ alkyl and/or hydroxyl radicals and chosen from pyrrolidine, piperidine, morpholine, piperazine and imidazole;

R''$_6$ represents:

a hydrogen atom;

a $C_1$-$C_{10}$ alkyl radical optionally substituted with a hydroxyl radical;

R''$_2$, R''$_3$, R''$_4$ and R''$_5$ each independently represent:

a hydrogen atom;

a $C_1$-$C_4$ alkyl radical.

According to a particular embodiment, the compound(s) of formula (I') or (II') are such that, when $Z''_1$ represents an oxygen atom, R''$_1$ denotes a linear or branched $C_1$-$C_6$ alkyl radical, a $C_1$-$C_6$ hydroxyalkyl radical; a di($C_1$-$C_4$ alkyl)amino($C_1$-$C_6$ alkyl) radical; a radical —[(CH$_2$)$_{m'}$—O]$_{p'}$-L'-Y' with p'=1, 2, 3, preferably 1 or 2, m'=2 or 3, L' denoting a saturated linear $C_1$-$C_6$ divalent hydrocarbon-based radical, and Y' denoting a hydroxyl radical or a hydrogen atom; an alkyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals such as methyl, or hydroxyl. Better still, R'$_1$ denotes a linear or branched saturated $C_1$-$C_6$ alkyl radical, such as a methyl, ethyl, n-propyl, isopropyl or tert-butyl radical; a $C_1$-$C_6$ hydroxyalkyl radical such as a hydroxyethyl or hydroxypropyl radical; a dimethylaminoethyl or dimethylaminopropyl radical; a radical —[(CH$_2$)$_2$—O]$_{p'}$-L'-Y' with p'=1 or 2, L' denoting a saturated, linear, $C_1$-$C_6$ divalent hydrocarbon-based radical, and Y' denoting a hydroxyl radical or a hydrogen atom such that -L'-Y' denotes an isopropyl or ethyl radical; or an ethyl or propyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals such as methyl, or hydroxyl.

According to a particular embodiment of the invention, the compound(s) of formula (I') or (II') are such that, when $Z''_1$ represents NH, R''$_1$ denotes a $C_1$-$C_6$ hydroxyalkyl radical, a di($C_1$-$C_4$ alkyl)amino($C_1$-$C_6$ alkyl) radical, an alkyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals such as methyl, or hydroxyl.

According to another embodiment, when $Z''_1$ represents —N(R''$_6$)—, R''$_1$ and R''$_6$ each independently denote a $C_1$-$C_6$ alkyl radical or a $C_1$-$C_6$ hydroxyalkyl radical, and preferably R'$_1$ and R'$_6$ are identical.

According to another embodiment, when $Z''_1$ is —N(R''$_6$)— and when R''$_1$ forms a ring with R''$_6$, this ring is chosen from pyrrolidinyl, piperidyl, morpholinyl and piperazinyl rings optionally substituted with one or more $C_1$-$C_4$ alkyl and/or hydroxyl radicals.

As examples of dyes of formula (I), (II), (I') and/or (II'), mention may be made of the compounds presented below:

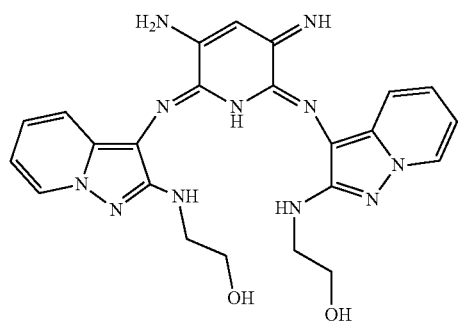

1

2,2′-[(5-amino-3-iminopyridine-2,6-(1H,3H)-
diylidene)bis(nitrilopyrazolo[1,5-a]
pyridine-3,2-diylimino)]diethanol

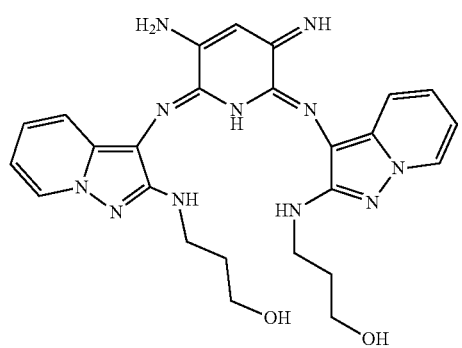

2

3,3′-[(5-amino-3-iminopyridine-2,6-(1H,3H)-
diylidene)bis(nitrilopyrazolo[1,5-a]
pyridine-3,2-diylimino)]dipropan-1-ol

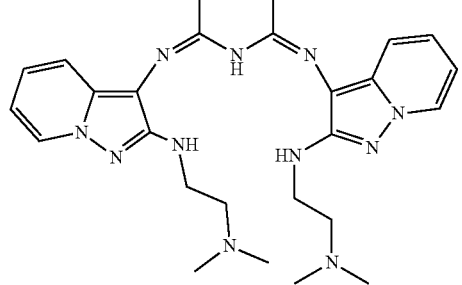

3

N3,N3′-(5-amino-3-iminopyridine-2,6-(1H,3H)-
diylidene)bis{N2-[2-(dimethylamino)ethyl]pyrazolo
[1,5-a]pyridine-2,3-diamine}

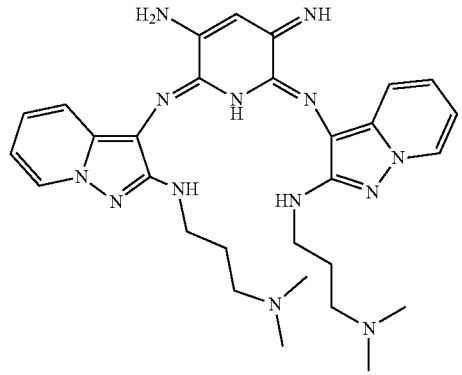

4

N3,N3′-(5-amino-3-iminopyridine-2,6-(1H,3H)-
diylidene)bis{N2-[3-(dimethylamino)propyl]pyrazolo
[1,5-a]pyridine-2,3-diamine}

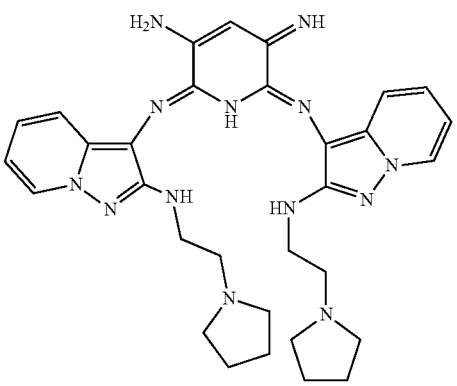

5

N3,N3′-(5-amino-3-iminopyridine-2,6-(1H,3H)-
diylidene)bis{N2-[2-(pyrrolidin-1-yl)ethyl]pyrazolo
[1,5-a]pyridine-2,3-diamine}

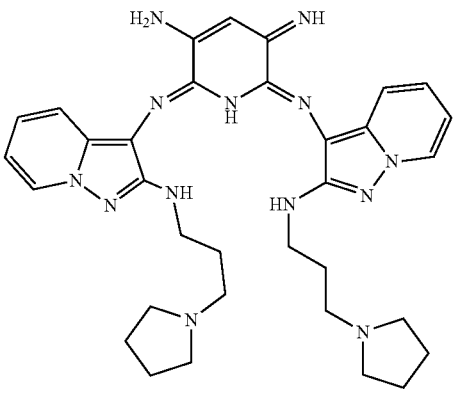

6

N3,N3′-(5-amino-3-iminopyridine-2,6-(1H,3H)-
diylidene)bis{N2-[3-(pyrrolidin-1-yl)propyl]pyrazolo
[1,5-a]pyridine-2,3-diamine}

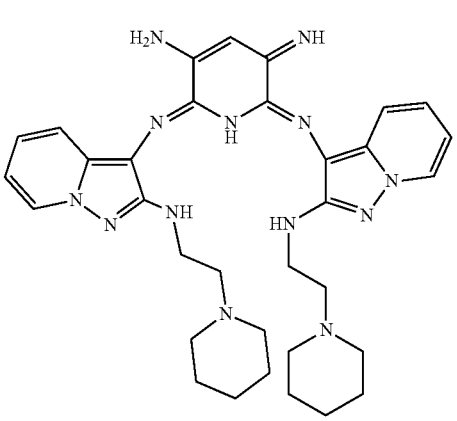

7

N3,N3′-(5-amino-3-iminopyridine-2,6-(1H,3H)-
diylidene)bis{N2-[2-(piperidin-1-yl)ethyl]
pyrazolo[1,5-a]pyridine-2,3-diamine}

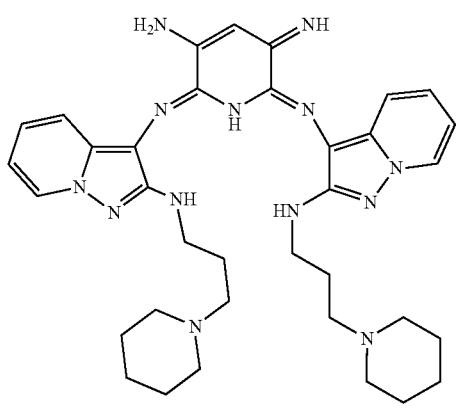

N3,N3'-(5-amino-3-iminopyridine-2,6-(1H,3H)-
diylidene)bis{N2-[3-(piperidin-1-yl)propyl]
pyrazolo[1,5-a]pyridine-2,3-diamine}

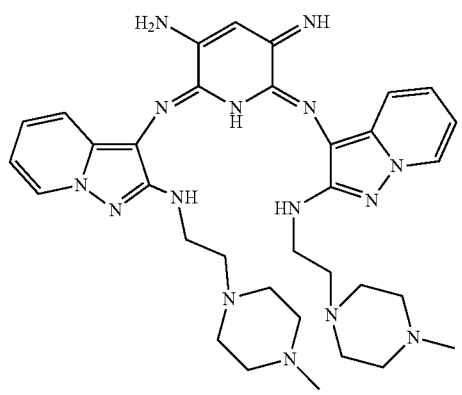

N3,N3'-(5-amino-3-iminopyridine-2,6-(1H,3H)-
diylidene)bis{N2-[2-(4-methylpiperazin-1-yl)
ethyl]pyrazolo[1,5-a]pyridine-2,3-diamine}

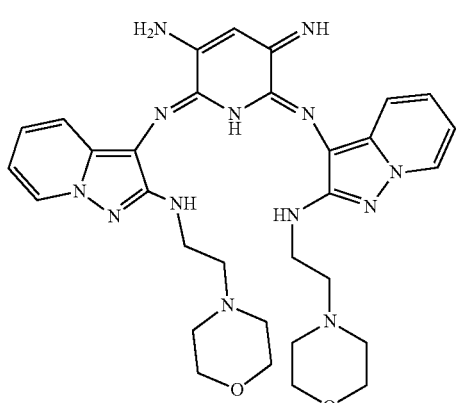

N3,N3'-(5-amino-3-iminopyridine-2-6-(1H,3H)-
diylidene)bis{N2-[2-(morpholin-4-yl)ethyl]
pyrazolo[1,5-a]pyridine-2,3-diamine}

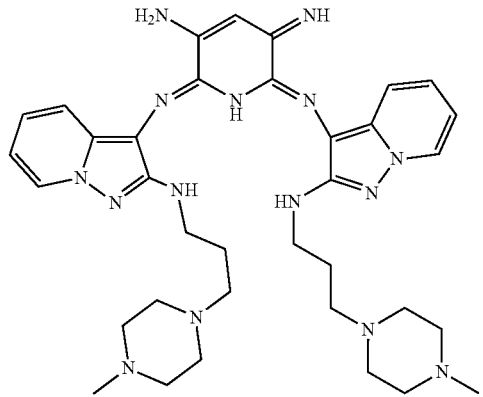

N3,N3'-(5-amino-3-iminopyridine-2,6-(1H,3H)-
diylidene)bis{N2-[3-(4-methylpiperazin-1-yl)
propyl]pyrazolo[1,5-a]pyridine-2,3-diamine}

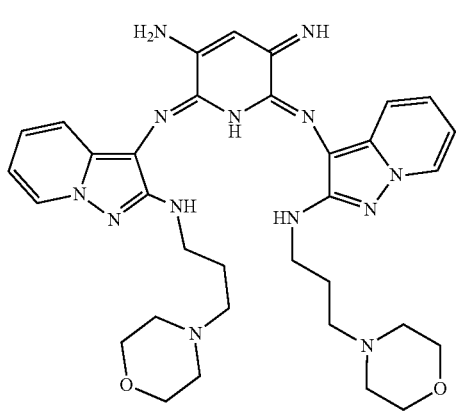

N3,N3'-(5-amino-3-iminopyridine-2,6-(1H,3H)-
diylidene)bis{N2-[3-(morpholin-4-yl)propyl]
pyrazolo[1,5-a]pyridine-2,3-diamine}

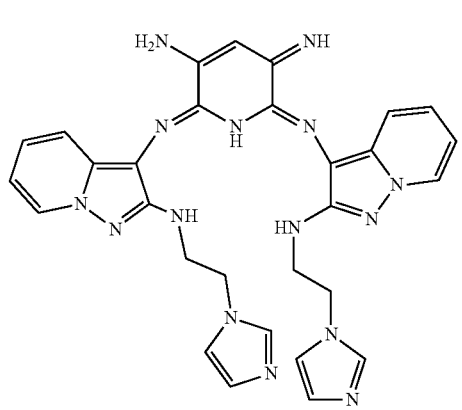

N3,N3'-(5-amino-3-iminopyridine-2,6-(1H,3H)-
diylidene)bis{N2-[2-(1H-imidazol-1-yl)ethyl]
pyrazolo[1,5-a]pyridine-2,3-diamine}

14

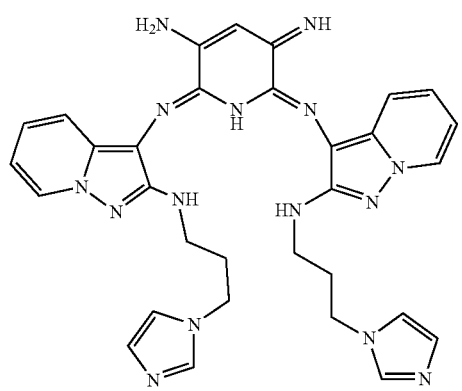

N3,N3'-(5-amino-3-iminopyridine-2,6-(1H,3H)-
diylidene)bis{N2-[3-(1H-imidazol-1-yl)
propyl]pyrazolo[1,5-a]pyridine-2,3-diamine}

15

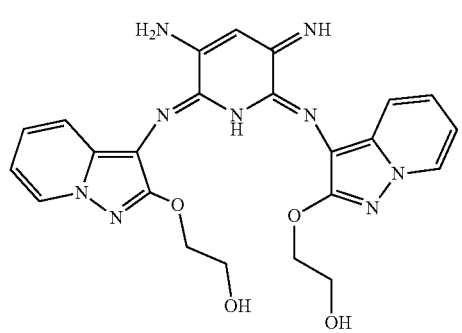

2,2'-[(5-amino-3-iminopyridine-2,6-(1H,3H)-
diylidene)bis(nitrilopyrazolo[1,5-a]
pyridine-3,2-diyloxy)]diethanol

16

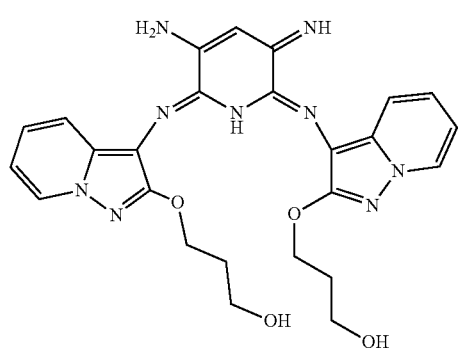

3,3'-[(5-amino-3-iminopyridine-2,6-(1H,3H)-
diylidene)bis(nitrilopyrazolo[1,5-a]
pyridine-3,2-diyloxy)]dipropan-1-ol

17

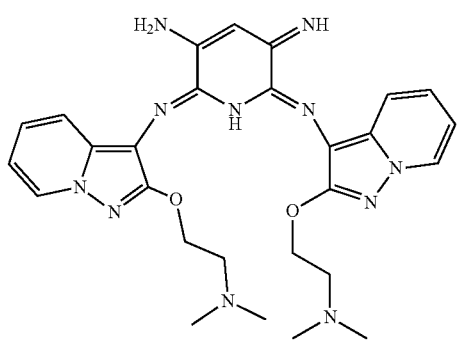

N,N'-(5-amino-3-iminopyridine-2,6-(1H,3H)-
diylidene)bis{2-[2-(dimethylamino)
ethoyx]pyrazolo[1,5-a]pyridin-3-amine}

18

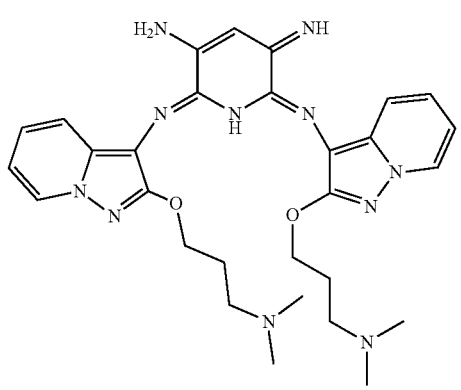

N,N'-(5-amino-3-iminopyridine-2,6-(1H,3H)-
diylidene)bis{2-[3-(dimethylamino)propoxy]
pyrazolo[1,5-a]pyridin-3-amine}

19

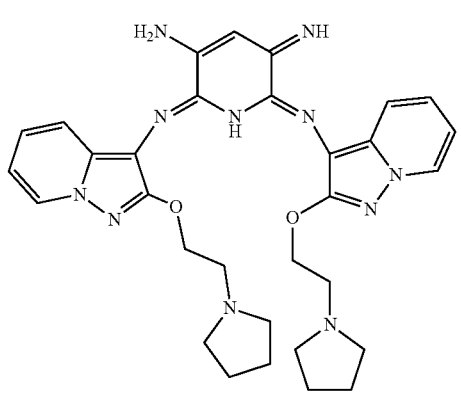

N,N'-(5-amino-3-iminopyridine-2,6-(1H,3H)-
diylidene)bis{2-[2-(pyrrolidin-1-yl)
ethoyx]pyrazolo[1,5-a]pyridin-3-amine}

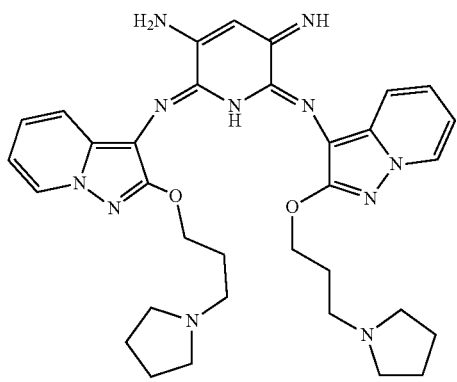

N,N′-(5-amino-3-iminopyridine-2,6-(1H,3H)-diylidene)bis{2-[3-(pyrrolidin-1-yl)propoxy]pyrazolo[1,5-a]pyridin-3-amine}

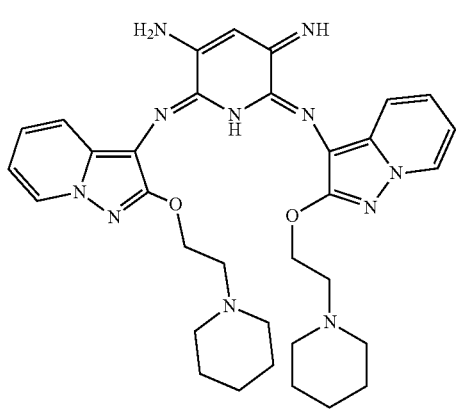

N,N′-(5-amino-3-iminopyridine-2,6-(1H,3H)-diylidene)bis{2-[2-(piperidin-1-yl)ethoxy]pyrazolo[1,5-a]pyridin-3-amine}

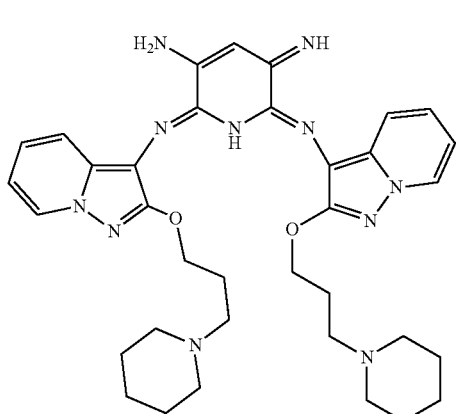

N,N′-(5-amino-3-iminopyridine-2,6-(1H,3H)-diylidene)bis{2-[3-(piperidin-1-yl)propoxy]pyrazolo[1,5-a]pyridin-3-amine}

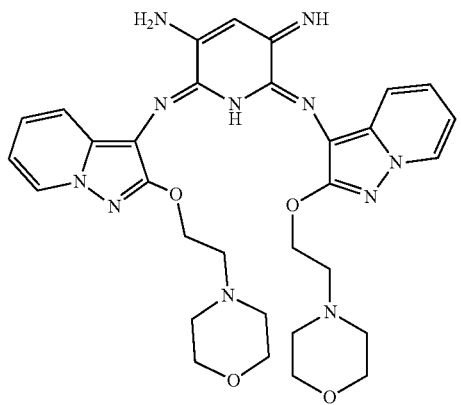

N,N′-(5-amino-3-iminopyridine-2,6-(1H,3H)-diylidene)bis{2-[2-(morpholin-4-yl)ethoxy]pyrazolo[1,5-a]pyridin-3-amine}

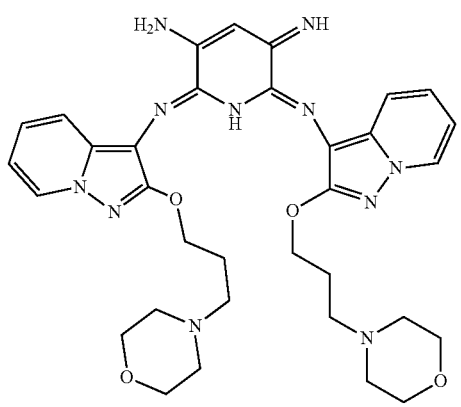

N,N′-(5-amino-3-iminopyridine-2,6-(1H,3H)-diylidene)bis{2-[3-(morpholin-4-yl)propoxy]pyrazolo[1,5-a]pyridin-3-amine}

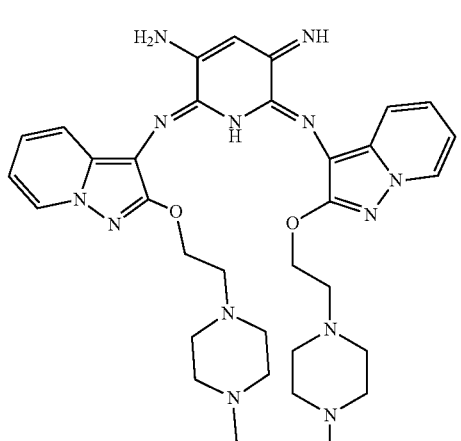

N,N′-(5-amino-3-iminopyridine-2,6-(1H,3H)-diylidene)bis{2-[2-(4-methylpiperazin-1-yl)ethoxy]pyrazolo[1,5-a]pyridin-3-amine}

27

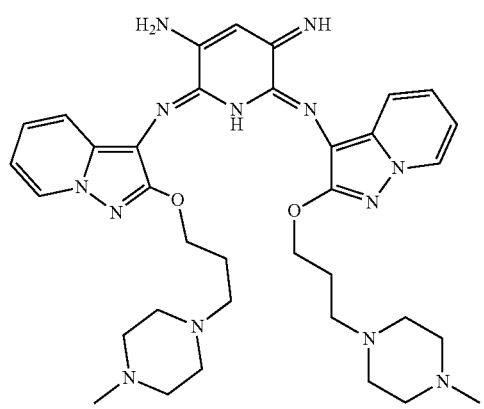

N,N'-(5-amino-3-iminopyridine-2,6-(1H,3H)-
diylidene)bis{2-[3-(4-methylpiperazin-1-yl)
propoxy]pyrazolo[1,5-a]pyridin-3-amine}

28

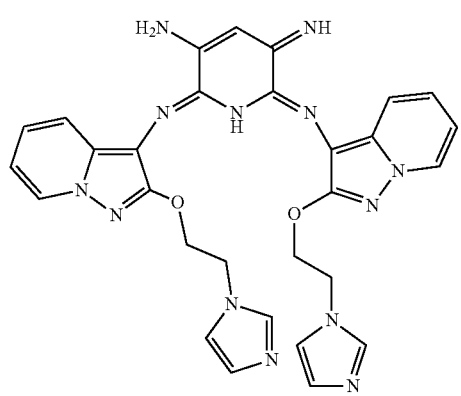

N,N'-(5-amino-3-iminopyridine-2,6-(1H,3H)-
diylidene)bis{2-[2-(1H-imidazol-1-yl)
ethoxy]pyrazolo[1,5-a]pyridin-3-amine}

29

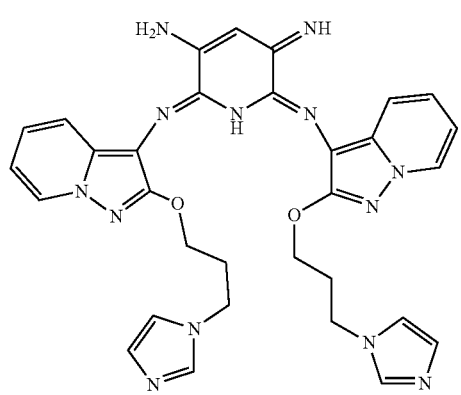

N,N'-(5-amino-3-iminopyridine-2,6-(1H,3H)-
diylidene)bis{2-[3-(1H-imidazol-1-yl)
propoxy]pyrazolo[1,5-a]pyridin-3-amine}

30

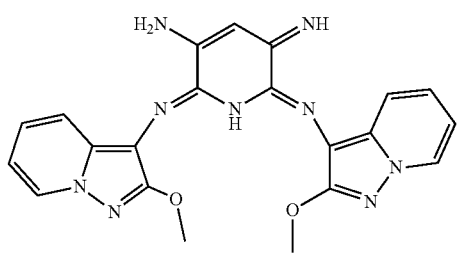

N,N'-(5-amino-3-iminopyridine-2,6-(1H,3H)-
diylidene)bis(2-methoxypyrazolo
[1,5-a]pyridin-3-amine)

31

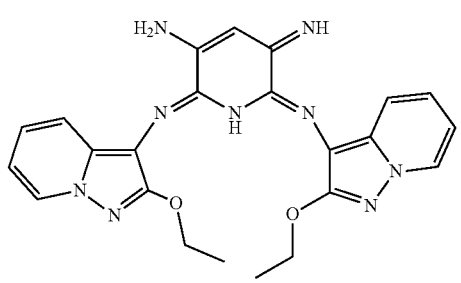

N,N'-(5-amino-3-iminopyridine-2,6-(1H,3H)-
diylidene)bis(2-ethoxypyrazolo
[1,5-a]pyridin-3-amine)

32

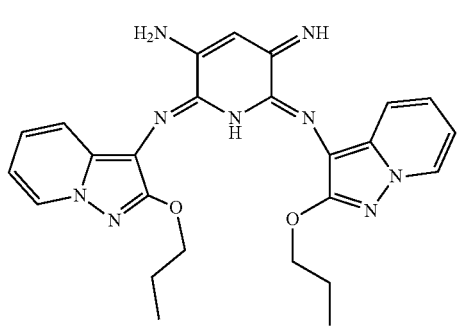

N,N'-(5-amino-3-iminopyridine-2,6-(1H,3H)-
diylidene)bis(2-propoxypyrazolo
[1,5-a]pyridin-3-amine)

33

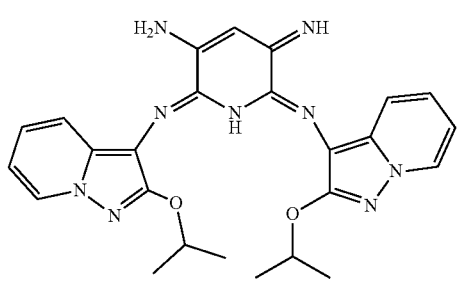

N,N'-(5-amino-3-iminopyridine-2,6-(1H,3H)-
diylidene)bis[2-(propan-2-yloxy)
pyrazolo[1,5-a]pyridin-3-amine]

34

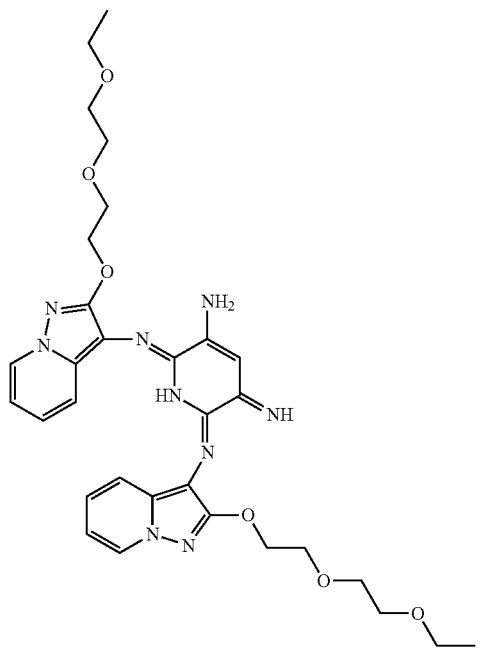

N,N′-(5-amino-3-iminopyridine-2,6-(1H,3H)-
diylidene)bis{2-[2-(2-ethoxyethoxy)ethoxy]-
6,7-dimethylpyrazolo[1,5-a]pyridin-3-amine}

35

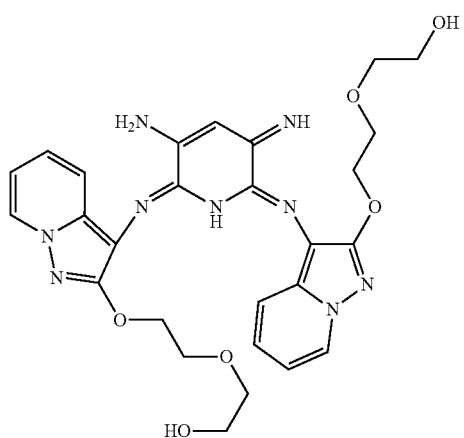

2-{2-[(3-{[3-amino-6-({2-[2-(2-hydroxyethoxy)
ethoxy]pyrazolo[1,5-a]pyridin-3-yl}amino)-5-imino-5,6-
dihydropyridin-2(1H)-ylidene]amino}pyrazolo
[1,5-a]pyridin-2-yl)oxy]ethoxy}ethanol

36

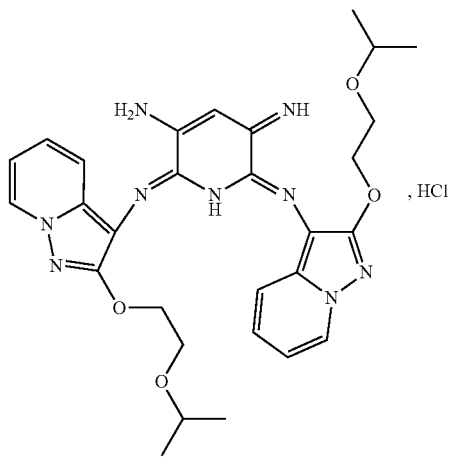

N,N′-(5-amino-3-iminopyridine-2,6-(1H,3H)-
diylidene)bis{2-[2-(propan-2-yloxy)ethoxy]
pyrazolo[1,5-a]pyridin-3-amine}

37

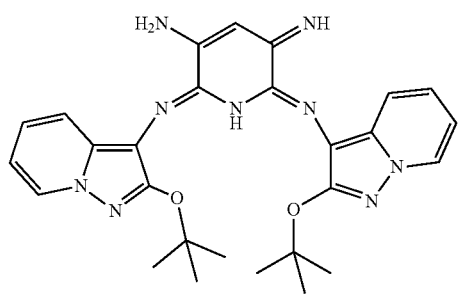

N,N′-(5-amino-3-iminopyridine-2,6-(1H,3H)-
diylidene)bis(2-tert-butoxypyrazolo
[1,5-a]pyridin-3-amine)

38

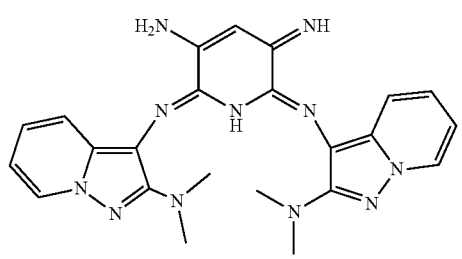

N3,N3′-(5-amino-3-iminopyridine-2,6-(1H,3H)-
diylidene)bis(N2,N2-dimethylpyrazolo
[1,5-a]pyridine-2,3-diamine)

39

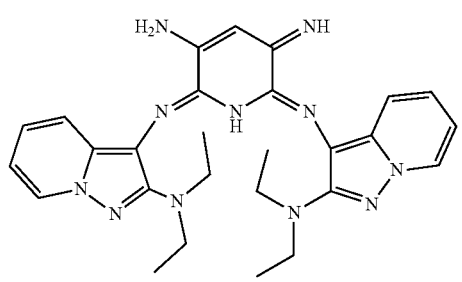

N3,N3′-(5-amino-3-iminopyridine-2,6-(1H,3H)-
diylidene)bis(N2,N2-diethylpyrazolo
[1,5-a]pyridine-2,3-diamine)

40

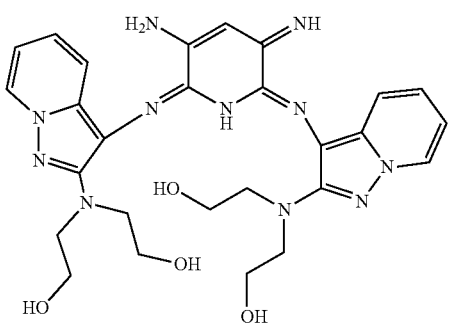

2,2′,2″,2‴-[(5-amino-3-iminopyridine-2,6-(1H,3H)-diylidene)bis(nitrilopyrazolo[1,5-a]pyridine-3,2-diylnitrilo)]tetraethanol

41

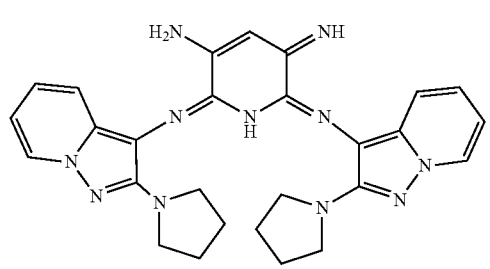

N,N′-(5-amino-3-iminopyridine-2,6-(1H,3H)-diylidene)bis[2-(pyrrolidin-1-yl)pyrazolo[1,5-a]pyridin-3-amine]

42

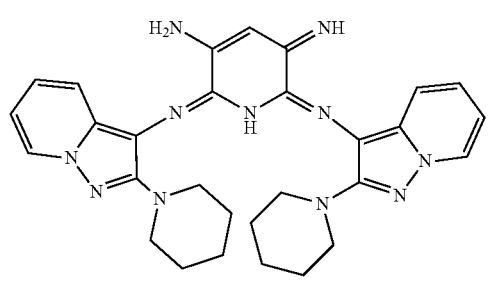

N,N′-(5-amino-3-iminopyridine-2,6-(1H,3H)-diylidene)bis[2-(piperidin-1-yl)pyrazolo[1,5-a]pyridin-3-amine]

43

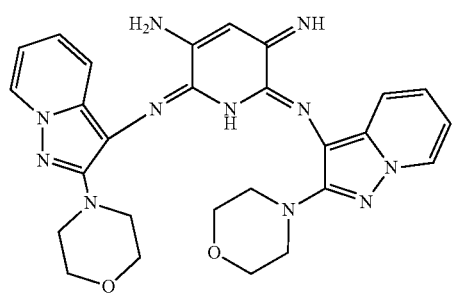

N,N′-(5-amino-3-iminopyridine-2,6-(1H,3H)-diylidene)bis[2-(morpholin-4-yl)pyrazolo[1,5-a]pyridin-3-amine]

44

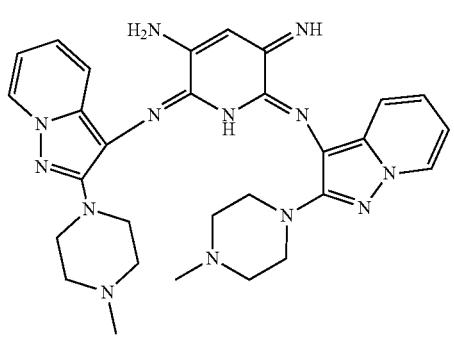

N,N′-(5-amino-3-iminopyridine-2,6-(1H,3H)-diylidene)bis[2-(4-methylpiperazin-1-yl)pyrazolo[1,5-a]pyridin-3-amine]

45

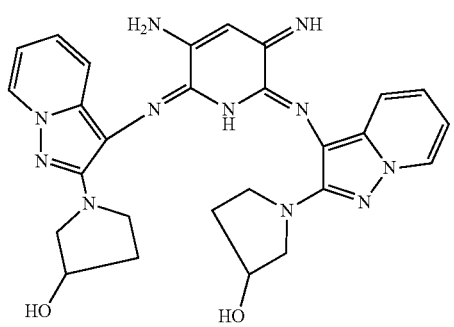

1,1′-(5-amino-3-iminopyridine-2,6-(1H,3H)-diylidene)bis(nitrilopyrazolo[1,5-a]pyridine-3,2-diyl)]dipyrrolidin-3-ol

46

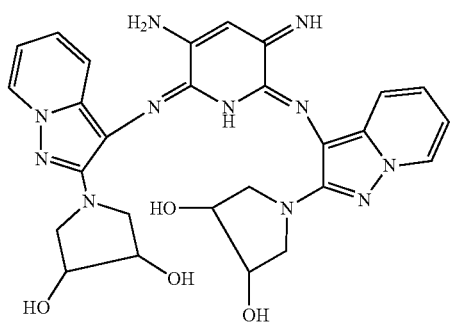

1,1′-[(5-amino-3-iminopyridine-2,6-(1H,3H)-diylidene)bis(nitrilopyrazolo[1,5-a]pyridine-3,2-diyl)]dipyrrolidine-3,4-diol

47

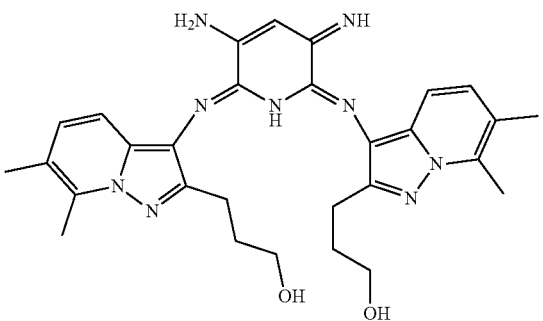

2,2′-{(5-amino-3-iminopyridine-2,6-(1H,3H)-diylidene)bis[nitrilo(6,7-dimethylpyrazolo[1,5-a]pyridine-3,2-diyl)imino]}diethanol

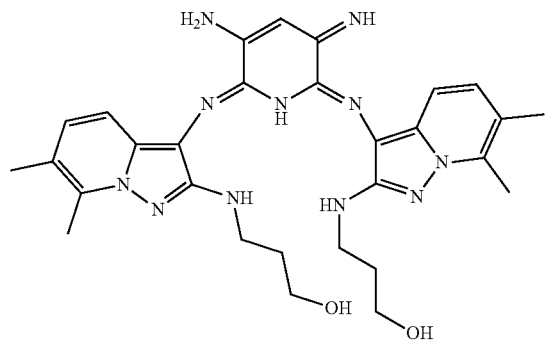

48

3,3′-{(5-amino-3-iminopyridine-2,6-(1H,3H)-
diylidene)bis[nitrilo(6,7-dimethylpyrazolo[1,5-a]
pyridine-3,2-diyl)imino]}dipropan-1-ol

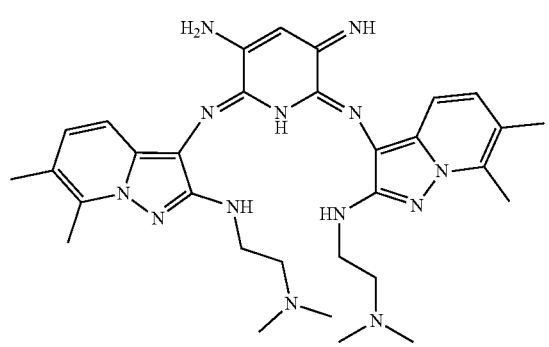

49

N3,N3′-(5-amino-3-iminopyridine-2,6-(1H,3H)-
diylidene)bis{N2-[2-(dimethylamino)ethyl]-6,7-
dimethylpyrazolo[1,5-a]pyridine-3,2-diamine}

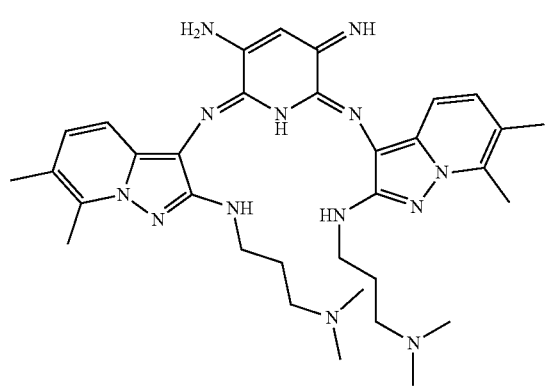

50

N3,N3′-(5-amino-3-iminopyridine-2,6-(1H,3H)-
diylidene)bis{N2-[3-(dimethylamino)propyl]-
6,7-dimethylpyrazolo[1,5-a]pyridine-2,3-diamine}

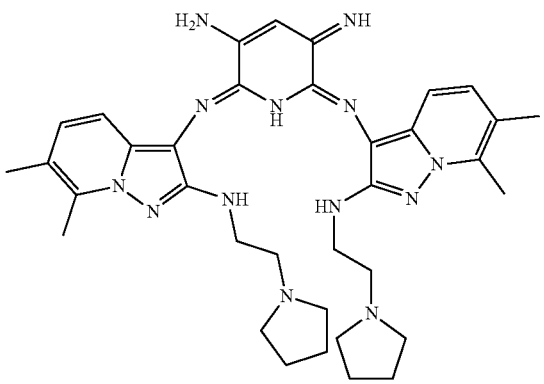

51

N3,N3′-(5-amino-3-iminopyridine-2,6-(1H,3H)-
diylidene)bis{6,7-dimethyl-N2-[2-(pyrrolidin-1-yl)
ethyl]pyrazolo[1,5-a]pyridine-3,2-diamine}

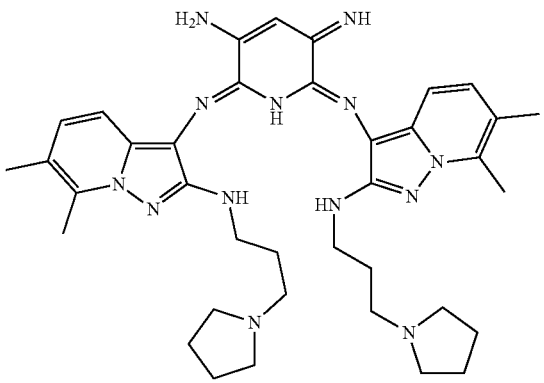

52

N3,N3′-(5-amino-3-iminopyridine-2,6-(1H,3H)-
diylidene)bis{6,7-dimethyl-N2-[3-(pyrrolidin-1-yl)
propyl]pyrazolo[1,5-a]pyridine-2,3-diamine}

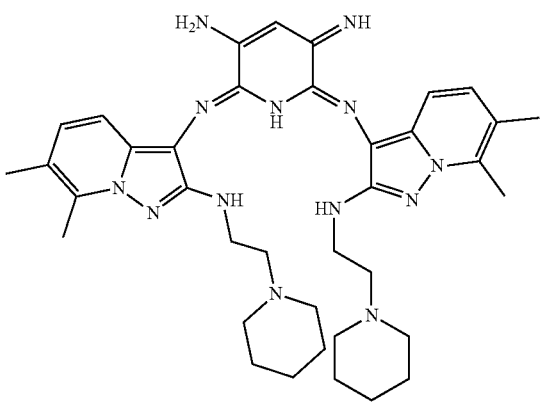

53

N3,N3′-(5-amino-3-iminopyridine-2,6-(1H,3H)-
diylidene)bis{6,7-dimethyl-N2-[2-(piperidin-1-yl)
ethyl]pyrazolo[1,5-a]pyridine-3,2-diamine}

54

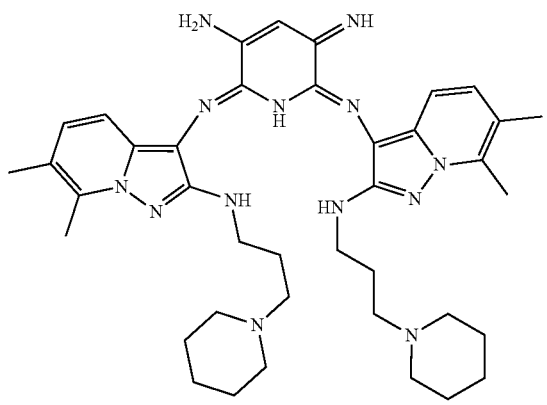

N3,N3'-(5-amino-3-iminopyridine-2,6-(1H,3H)-
diylidene)bis{6,7-dimethyl-N2-[3-(piperidin-1-yl)
propyl]pyrazolo[1,5-a]pyridine-2,3-diamine}

55

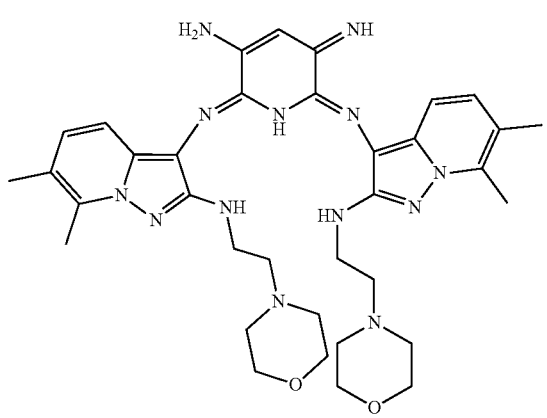

N3,N3'-(5-amino-3-iminopyridine-2,6-(1H,3H)-
diylidene)bis{6,7-dimethyl-N2-[2-(morpholin-4-yl)
ethyl]pyrazolo[1,5-a]pyridine-2,3-diamine}

56

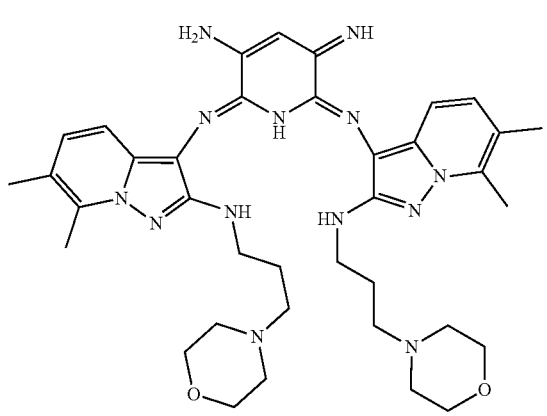

N3,N3'-(5-amino-3-iminopyridine-2,6-(1H,3H)-
diylidene)bis{6,7-dimethyl-N2-[3-(morpholin-4-yl)
propyl]pyrazolo[1,5-a]pyridine-2,3-diamine}

57

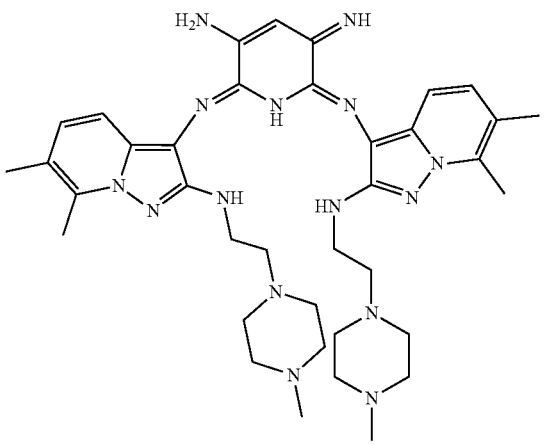

N3,N3'-(5-amino-3-iminopyridine-2,6-(1H,3H)-
diylidene)bis{6,7-dimethyl-N2-[2-(4-methylpiperazin-
1-yl)ethyl]pyrazolo[1,5-a]pyridine-2,3-diamine}

58

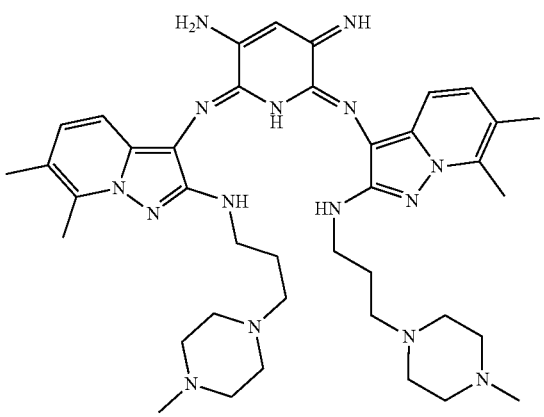

N3,N3'-(5-amino-3-iminopyridine-2,6-(1H,3H)-
diylidene)bis{6,7-dimethyl-N2-[3-(4-methylpiperazin-
1-yl)propyl]pyrazolo[1,5-a]pyridine-2,3-diamine}

59

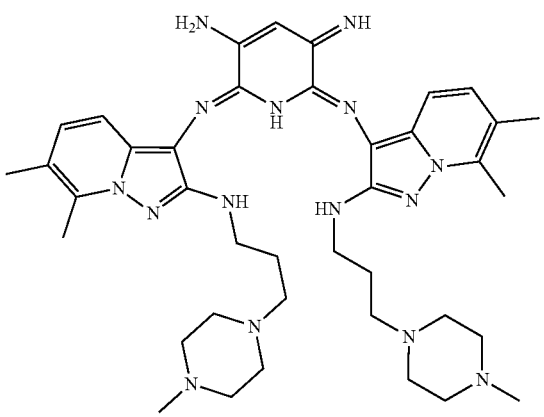

N3,N3'-(5-amino-3-iminopyridine-2,6-(1H,3H)-
diylidene)bis{N2-[2-(1H-imidazol-1-yl)ethyl]-6,7-
dimethylpyrazolo[1,5-a]pyridine-2,3-diamine}

60

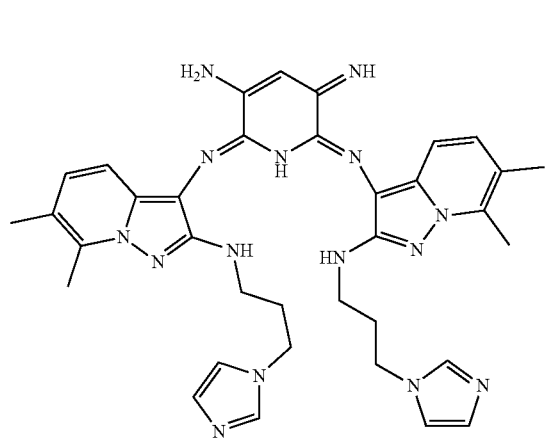

N3,N3'-(5-amino-3-iminopyridine-2,6-(1H,3H)-diylidene)bis{N2-[3-(1H-imidazol-1-yl)proply]-6,7-dimethylpyrazolo[1,5-a]pyridine-2,3-diamine}

61

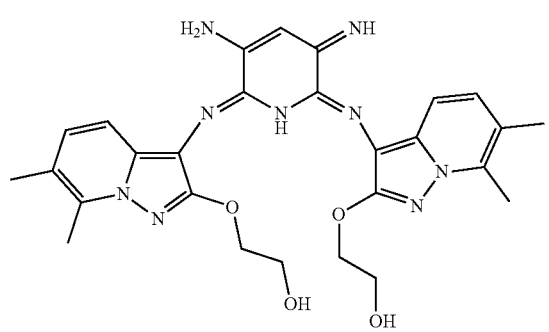

2,2'-{(5-amino-3-iminopyridine-2,6-(1H,3H)-diylidene)bis[nitrilo(6,7-dimethylpyrazolo[1,5-a]pyridine-3,2-diyl)oxy]}diethanol

62

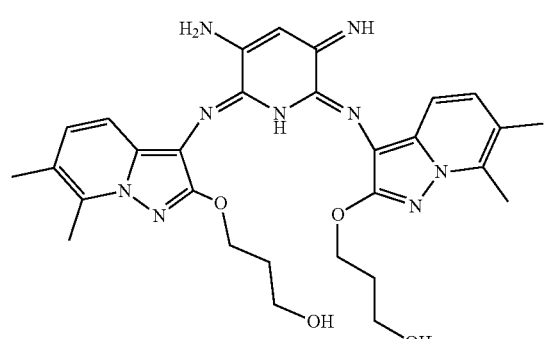

3,3'-{(5-amino-3-iminopyridine-2,6-(1H,3H)-diylidene)bis[nitrilo(6,7-dimethylpyrazolo[1,5-a]pyridine-3,2-diyl)oxy]}dipropan-1-ol

63

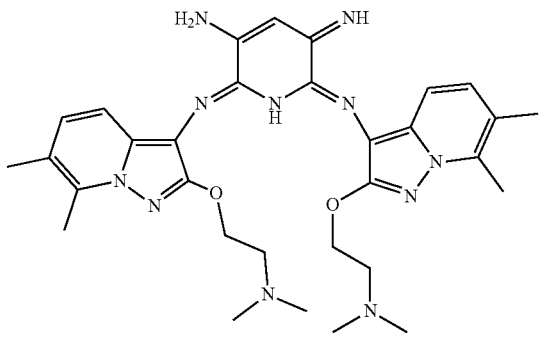

N,N'-(5-amino-3-iminopyridine-2,6-(1H,3H)-diylidene)bis{2-[2-(dimethylamino)ethoxy]-6,7-dimethylpyrazolo[1,5-a]pyridin-3-amine}

64

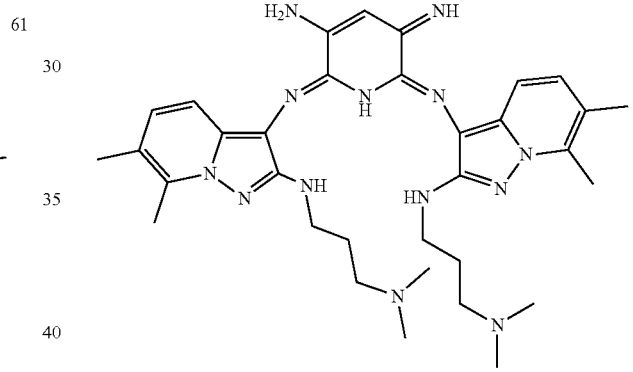

N3,N3'-(5-amino-3-iminopyridine-2,6-(1H,3H)-diylidene)bis{N2-[3-(dimethylamino)propyl]-6,7-dimethylpyrazolo[1,5-a]pyridine-2,3-diamine}

65

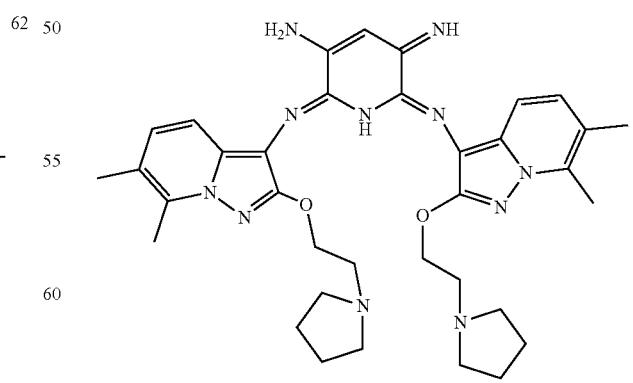

N3,N3'-(5-amino-3-iminopyridine-2,6-(1H,3H)-diylidene)bis{6,7-dimethyl-N2-[2-(pyrrolidin-1-yl)ethyl]pyrazolo[1,5-a]pyridine-2,3-diamine}

-continued

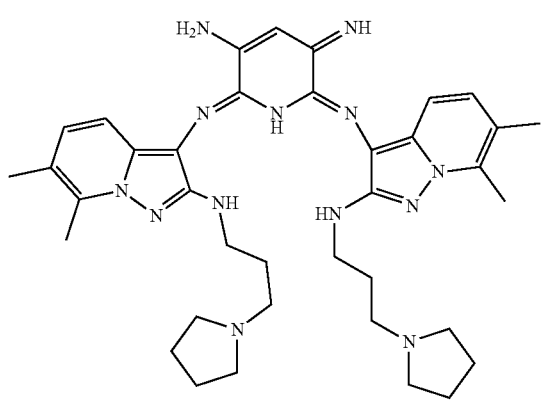

66

N,N′-(5-amino-3-iminopyridine-2,6-(1H,3H)-
diylidene)bis{6,7-dimethyl-2-[3-(pyrrolidin-1-yl)
propoxy]pyrazolo[1,5-a]pyridin-3-amine}

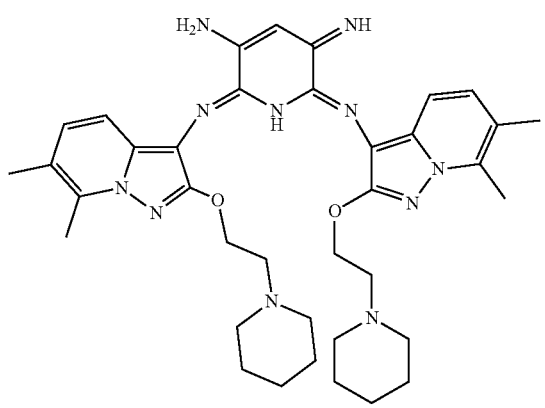

67

N,N′-(5-amino-3-iminopyridine-2,6-(1H,3H)-
diylidene)bis{6,7-dimethyl-2-[2-(piperidin-1-yl)
ethoxy]pyrazolo[1,5-a]pyridin-3-amine}

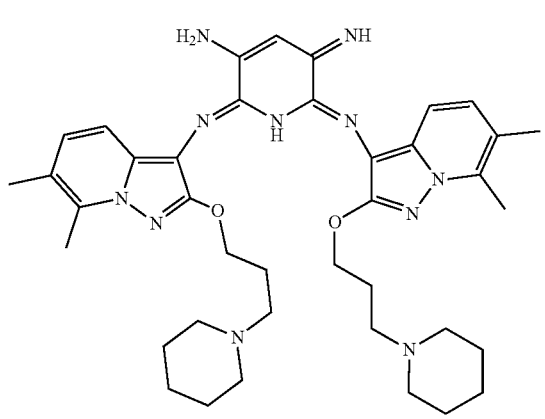

68

N,N′-(5-amino-3-iminopyridine-2,6-(1H,3H)-
diylidene)bis{6,7-dimethyl-2-[3-(piperidin-1-yl)
propoxy]pyrazolo[1,5-a]pyridin-3-amine}

-continued

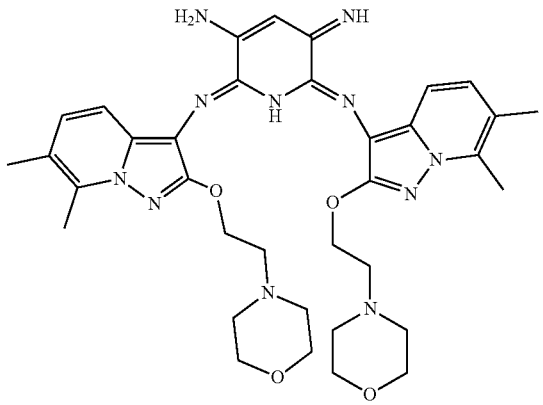

69

N,N′-(5-amino-3-iminopyridine-2,6-(1H,3H)-
diylidene)bis{6,7-dimethyl-2-[2-(morpholin-4-yl)
ethoxy]pyrazolo[1,5-a]pyridin-3-amine}

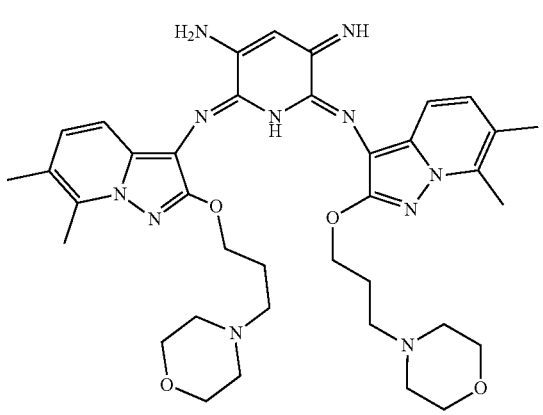

70

N,N′-(5-amino-3-iminopyridine-2,6-(1H,3H)-
diylidene)bis{6,7-dimethyl-2-[3-(morpholin-4-yl)
propoxy]pyrazolo[1,5-a]pyridin-3-amine}

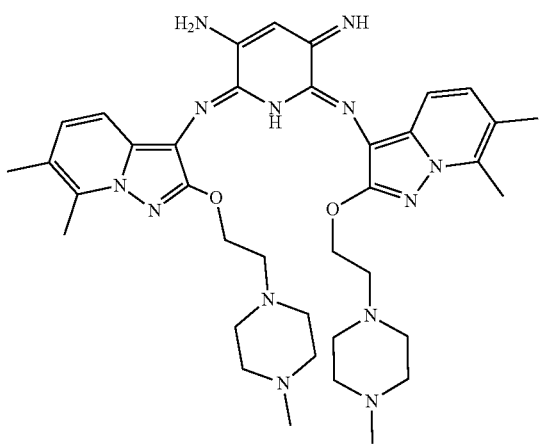

71

N,N′-(5-amino-3-iminopyridine-2,6-(1H,3H)-
diylidene)bis{6,7-dimethyl-2-[2-(4-methylpiperazin-
1-yl)ethoxy]pyrazolo[1,5-a]pyridin-3-amine}

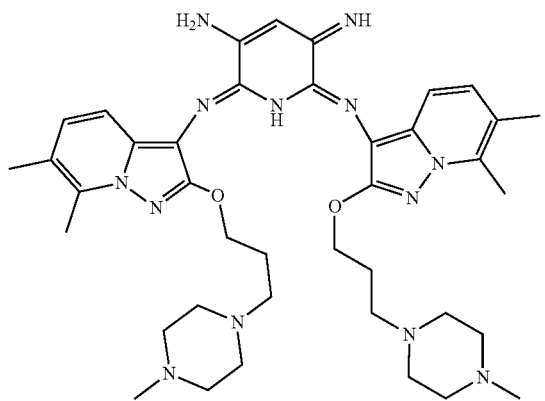

N,N′-(5-amino-3-iminopyridine-2,6-(1H,3H)-
diylidene)bis{6,7-dimethyl-2-[3-(4-methylpiperazin-
1-yl)propoxy]pyrazolo[1,5-a]pyridin-3-amine}

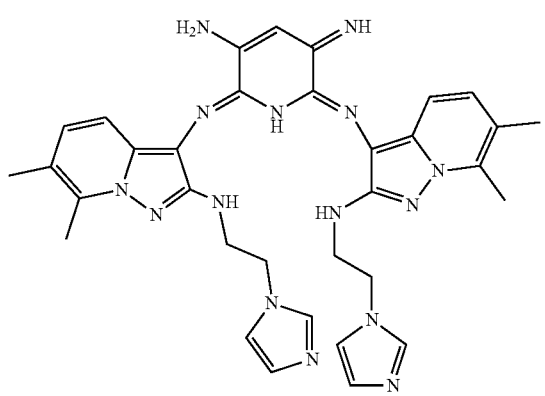

N,N′-(5-amino-3-iminopyridine-2,6-(1H,3H)-
diylidene)bis{2-[2-(1H-imidazol-1-yl)ethoxy]-6,7-
dimethylpyrazolo[1,5-a]pyridin-3-amine}

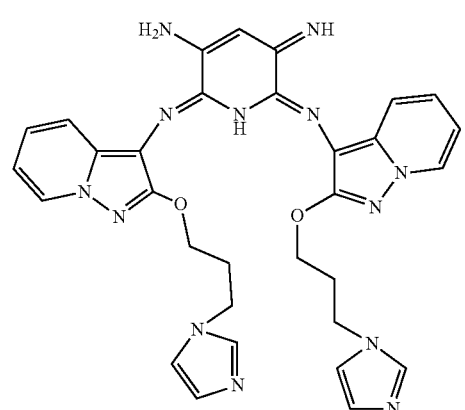

N,N′-(5-amino-3-iminopyridine-2,6-(1H,3H)-
diylidene)bis{2-[3-(1H-imidazol-1-yl)propoxy]-6,7-
dimethylpyrazolo[1,5-a]pyridin-3-amine}

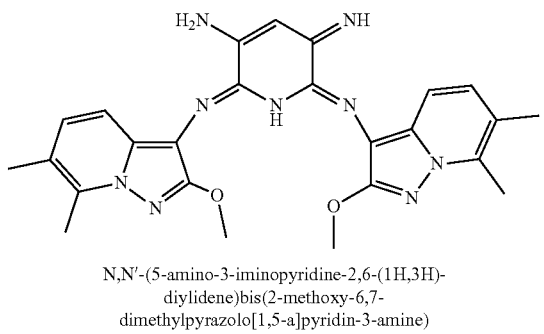

N,N′-(5-amino-3-iminopyridine-2,6-(1H,3H)-
diylidene)bis(2-methoxy-6,7-
dimethylpyrazolo[1,5-a]pyridin-3-amine)

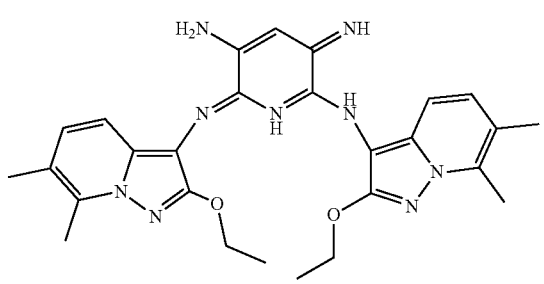

N2-(2-ethoxy-6,7-dimethylpyrazolo[1,5-a]pyridin-3-yl)-
6-[(2-ethoxy-6,7-dimethylpyrazolo[1,5-a]pyridin-3-yl)
imino]-3-imino-3,6-dihydropyridine-2,5-diamine

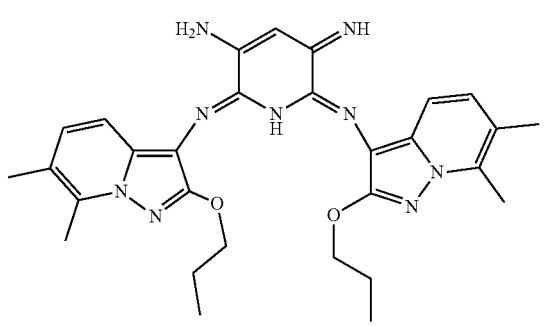

N,N′-(5-amino-3-iminopyridine-2,6-(1H,3H)-
diylidene)bis(6,7-dimethyl-
2-propoxypyrazolo[1,5-a]pyridin-3-amine)

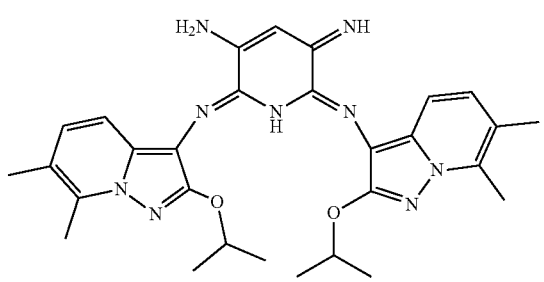

N,N′-(5-amino-3-iminopyridine-2,6-(1H,3H)-
diylidene)bis[6,7-dimethyl-2-(propan-2-yloxy)
pyrazolo[1,5-a]pyridin-3-amine]

79

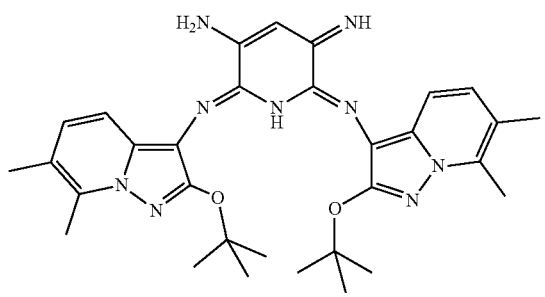

N,N'-(5-amino-3-iminopyridine-2,6-(1H,3H)-
diylidene)bis(2-tert-butoxy-6,7-
dimethylpyrazolo[1,5-a]pyridin-3-amine)

80

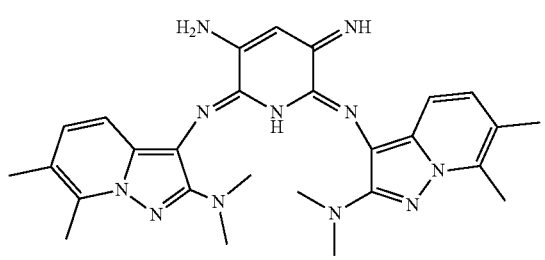

N3,N3'-(5-amino-3-iminopyridine-2,6-(1H,3H)-
diylidene)bis(N2,N2,6,7-tetramethylpyrazolo
[1,5-a]pyridine-2,3-diamine)

81

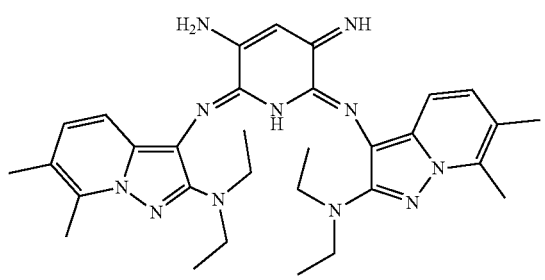

N3,N3'-(5-amino-3-iminopyridine-2,6-(1H,3H)-
diylidene)bis(N2,N2-diethyl-6,7-dimethylpyrazolo
[1,5-a]pyridine-2,3-diamine)

82

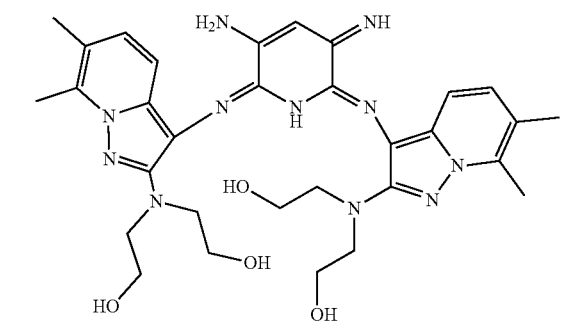

2,2',2'',2'''-{(5-amino-3-iminopyridine-2,6-
(1H,3H)-diylidene)bis[nitrilo(6,7-dimethylpyrazolo
[1,5-a]pyridine-3,2-diyl)nitrilo]}tetraethanol

83

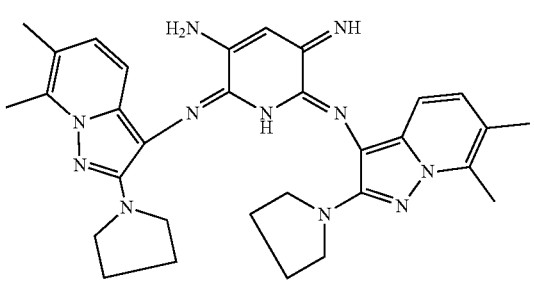

N,N'-(5-amino-3-iminopyridine-2,6-(1H,3H)-
diylidene)bis[6,7-dimethyl-2-(pyrrolidin-1-yl)
pyrazolo[1,5-a]pyridin-3-amine]

84

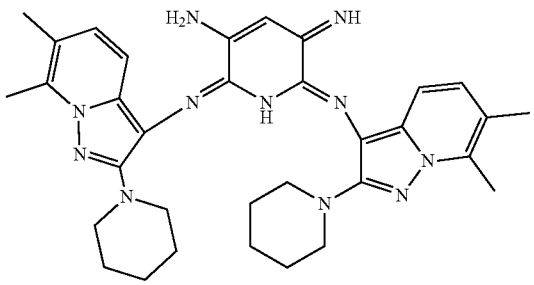

N,N'-(5-amino-3-iminopyridine-2,6-(1H,3H)-
diylidene)bis[6,7-dimethyl-2-(piperidin-1-yl)
pyrazolo[1,5-a]pyridin-3-amine]

85

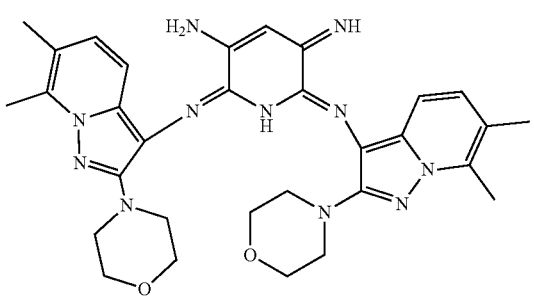

N,N'-(5-amino-3-iminopyridine-2,6-(1H,3H)-
diylidene)bis[6,7-dimethyl-2-(morpholin-4-yl)
pyrazolo[1,5-a]pyridin-3-amine]

86

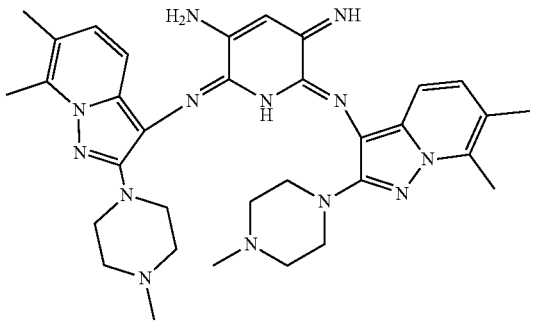

N,N'-(5-amino-3-iminopyridine-2,6-(1H,3H)-
diylidene)bis[6,7-dimethyl-2-(4-methylpiperazin-
1-yl)pyrazolo[1,5-a]pyridin-3-amine]

-continued

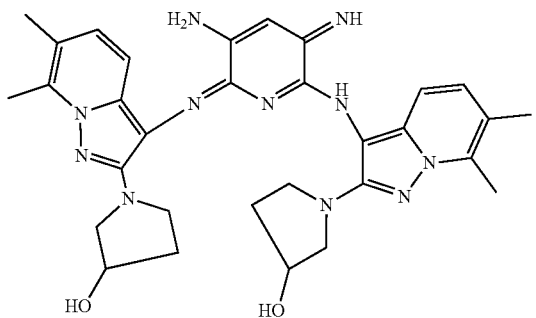

1,1'-{(5-amino-3-iminopyridine-2,6-(1H,3H)-diylidene)bis[nitrilo(6,7-dimethylpyrazolo[1,5-a]pyridine-3,2-diyl)]}dipyrrolidin-3-ol

87

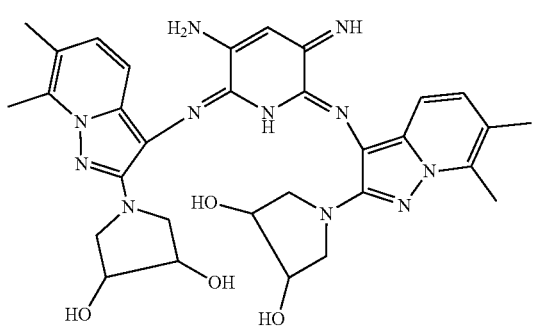

1,1'-{(5-amino-3-iminopyridine-2,6-(1H,3H)-diylidene)bis[nitrilo(6,7-dimethylpyrazolo[1,5-a]pyridine-3,2-diyl)]}dipyrrolidine-3,4-diol

88 and also the leuco forms thereof, the optical isomers, geometrical isomers, tautomers, solvates and addition salts thereof.

Another subject of the invention is a process for preparing compounds of formulae (I) and (II) as defined previously, according to the following scheme:

A) in the case where formulae (I) and (II) are symmetrical:

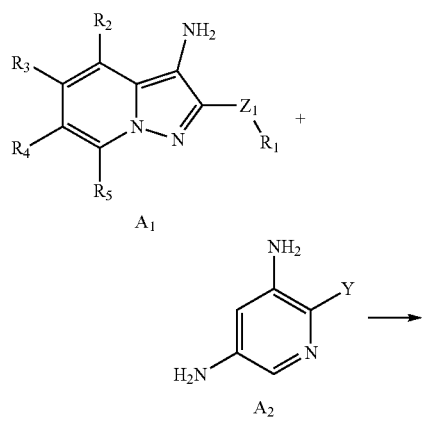

-continued

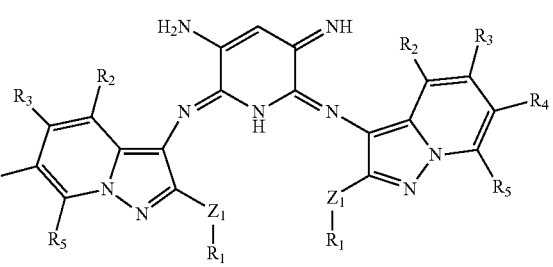

(I)

+

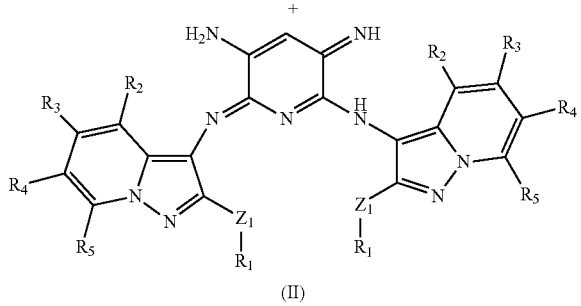

(II)

which consists:

a) in a first stage, in reacting at least two molar equivalents of pyrazolo[1,5-a]pyridine compound $A_1$ comprising an amino group in position 3 with a pyridine compound $A_2$ which is free in position 6 and comprising in position 2 either a hydrogen atom or an electrofugal group, preferably, this reaction is performed i) in a polar protic solvent such as in water or a mixture of water/$C_1$-$C_{10}$ alcohol such as ethanol, ii) and/or in the presence of one or more mineral or organic basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between room temperature, i.e. 25° C., and the reflux temperature of the solvent, preferably at room temperature; and then b) in a second stage, in maintaining the reaction medium under stirring for a time of between 5 minutes and 48 hours, more particularly between 30 minutes and 24 hours if the reaction is performed at room temperature; and then c) the reaction products (I) and (II) are optionally purified via a standard technique such as recrystallization, filtration or chromatography;

it being understood that, in formulae $A_1$, $A_2$, (I) and (II), the radicals $R_1$ to $R_5$ and $Z_1$ are as defined previously and Y represents a hydrogen atom or an electrofugal group, preferably an electrofugal group such as halogen, (poly)halo($C_1$-$C_6$ alkoxy), or (poly)(halo)($C_1$-$C_6$ alkyl)-$SO_3$—;

B) in the case where formulae (I) and (II) are symmetrical or dissymmetrical:

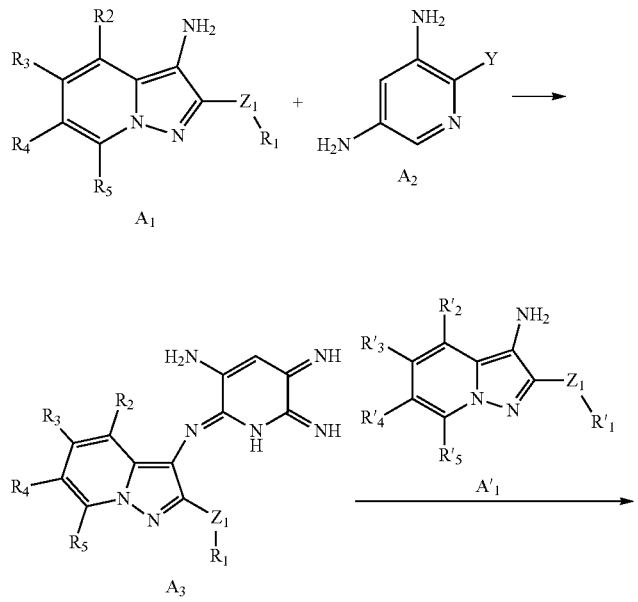

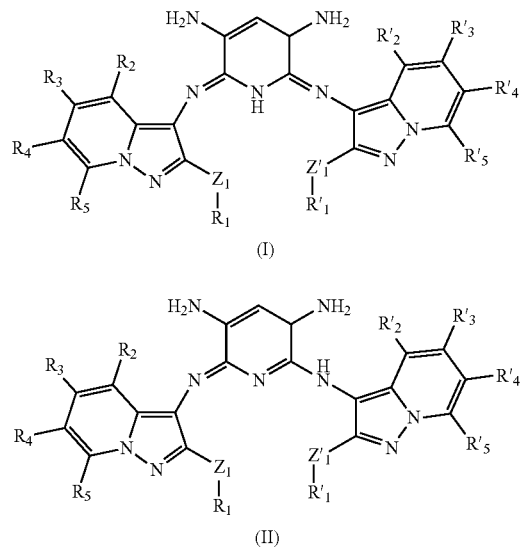

which consists:
- a) in a first stage, in reacting one molar equivalent of pyrazolo[1,5-a]pyridine compound $A_1$ comprising an amino group in position 3 with a pyridine compound $A_2$ which is free in position 6 and comprising in position 2 either a hydrogen atom or an electrofugal group, preferably, this reaction is performed i) in a polar protic solvent such as in water or a mixture of water/$C_1$-$C_{10}$ alcohol such as ethanol, ii) and/or in the presence of one or more mineral or organic basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between room temperature, i.e. 25° C., and the reflux temperature of the solvent, preferably at room temperature; and then
- b) in a second stage, in maintaining the reaction medium under stirring for a time of between 5 minutes and 48 hours, more particularly between 30 minutes and 24 hours if the reaction is performed at room temperature; and then
- c) the reaction product $A_3$ is optionally purified via a standard technique such as recrystallization, filtration or chromatography;
- d) according to a variant, compound $A_3$ once purified reacts with a molar equivalent of pyrazolo[1,5-a]pyridine compound $A'_1$ comprising an amino group in position 3, under the same conditions as steps a) and b), to give the products (I) and (II), which are optionally purified via a standard technique such as recrystallization, filtration or chromatography;
- d) according to another variant, compound $A_3$ is not purified, and reacts with a molar equivalent of pyrazolo[1,5-a]pyridine compound $A'_1$ comprising an amino group in position 3, under the same conditions as steps a) and b), to give the products (I) and (II), which are optionally purified via a standard technique such as recrystallization, filtration or chromatography;

it being understood that, in formulae $A_1$, $A_2$, $A_3$, (I) and (II), the radicals $R_1$ to $R_5$, $Z_1$, $R'_1$ to $R'_5$, Y and $Z'_1$ are as defined previously.

More particularly, the compounds of formula (I) and/or (II) may be obtained according to the procedure described below.

In a reactor, compound $A_1$ is dissolved in water and/or ethanol at room temperature. Compound $A_2$ is then added, followed by a base such as ammonia, sodium hydroxide, potassium hydroxide, a mineral carbonate such as potassium carbonate, or a sodium or potassium or ammonium acetate in the presence of an oxidizing agent. The oxidizing agent may be air, aqueous hydrogen peroxide solution or any other chemical oxidizing agent. The reaction medium becomes coloured as soon as the last two reagents are added. The reaction medium thus obtained is stirred for a time of from 30 minutes to 6 days. The product formed is filtered off and then washed with water and then optionally with isopropyl ether. The compound recovered in powder form is dried at 20° C. under vacuum to constant weight. In the case where there is no precipitation, the compound resulting from this reaction is recovered by evaporating off the solvent and optionally purified on a column of silica.

The characterization is performed by NMR spectroscopy and/or mass spectrometry.

A subject of the present invention is also a composition for dyeing keratin fibres, comprising, in a medium that is suitable especially for dyeing keratin fibres such as the hair, at least one compound chosen from the compounds of formulae (I) and/or (II) as defined previously, and also the leuco forms, optical isomers, geometrical isomers and tautomers thereof, and also the addition salts thereof with an acid or a base, and the solvates thereof such as hydrates.

According to a particular embodiment of the invention, the compounds of formula (I), (II), (I') or (II') as defined previously represent from 0.01% to 15% and more particularly from 0.05% to 10% by weight relative to the total weight of the composition.

The dye composition that is useful in the context of the invention may furthermore comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines, examples that may be mentioned more particularly include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]propyl}-3-methyl-1H-imidazol-3-ium chloride, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]-propyl}-3-methyl-1H-imidazol-3-ium chloride, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives, and derivatives of pyrazolo [1,2-a]pyrazol-1-one type and derivatives of pyrazolopyridine type as described in European patent applications Nos 1 792 903 and 1 792 606.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made of the compounds described, for example, in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo [1,5-a]pyrimidine-3,5-diamine, 3-aminopyrazolo[1,5-a]pyrimidin-7-ol, 3-aminopyrazolo-[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a] pyrimidine-3,7-diamine, 2,5,-N7,N7-tetra-methylpyrazolo [1,5-a]pyrimidine-3,7-diamine and 3-amino-5-methyl-7-imidazolyl-propylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1- tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the derivatives of pyrazolo[1,2a]pyrazol-1-one type, mention may be made of compounds such as 2,3-diamino-6,7-dihydro,1H-5H-pyrazolo[1,2a]pyrazol-1-one.

The dye composition that is useful in the context of the invention may also contain one or more couplers that are conventionally used for dyeing keratin fibres. Among these couplers, mention may be made especially of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In general, the addition salts with an acid that may be used in the context of the invention for the oxidation bases and the couplers are especially chosen from the hydrochlorides, hydrobromides, sulfates, citrates, succinates, tartrates, lactates, tosylates, benzenesulfonates, phosphates and acetates.

When the oxidation base(s) are present in the dye composition according to the invention, their amount preferably ranges from 0.001% to 10% by weight and more preferentially from 0.005% to 6% by weight relative to the total weight of the composition.

When they are present, the coupler(s) are generally present in an amount ranging from 0.001% to 10% by weight and even more preferentially from 0.005% to 6% by weight relative to the total weight of the composition.

The dye composition that is useful in the context of the invention may optionally comprise at least one additional direct dye conventionally used for the dyeing of keratin fibres. It may be chosen from cationic and nonionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanin dyes, triarylmethane-based dyes and natural dyes, alone or as mixtures.

It may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)-aminobenzene, 1,4-diamino-2-nitrobenzene, 1-amino-2-nitro-4-methylamino-benzene, N-(β-hydroxyethyl)-2-nitro-para-phenylenediamine, 1-amino-2-nitro-4-(β-hydroxyethyl)amino-5-chlorobenzene, 2-nitro-4-amino-diphenylamine, 1-amino-3-nitro-6-hydroxybenzene, 1-(β-aminoethyl)amino-2-nitro-4-(β-hydroxyethyloxy)-benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenyl-amine and 1-amino-2-nitro-4-hydroxy-5-methylbenzene.

The additional direct dye may also be chosen from yellow and green-yellow nitrobenzene direct dyes. Examples that may be mentioned include the compounds chosen from: 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxyl-methyl)methyl]amino-5-nitrobenzene, 1-(β-hydroxyethyl)amino-2-nitrobenzene and 4-(β-hydroxyethyl)amino-3-nitrobenzamide.

Mention may also be made of blue or violet nitrobenzene direct dyes, for instance 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl-N-β-hydroxyethyl)amino-2-nitrobenzene, 1-(β-hydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, and the 2-nitro-para-phenylenediamines of formula (III) below:

in which:
$R_B$ represents a $C_1$-$C_4$ alkyl radical or a β-hydroxyethyl, β-hydroxypropyl or γ-hydroxypropyl radical;
$R_A$ and $R_C$, which may be identical or different, represent a β-hydroxyethyl, β-hydroxypropyl, γ-hydroxypropyl or β,γ-dihydroxypropyl radical, at least one of the radicals $R_B$, $R_C$ or $R_A$ representing a γ-hydroxypropyl radical and $R_B$ and $R_C$ not being able simultaneously to denote a β-hydroxyethyl radical when $R_B$ is a γ-hydroxypropyl radical, such as those described in French patent FR 2 692 572.

Among the azo direct dyes that may be used according to the invention, mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these compounds, mention may be made most particularly of the following dyes: 1,3-dimethyl-2-[[4-(dimethylamino)phenyl]azo]-1H-imidazolium halides, 1,3-dimethyl-2-[(4-aminophenyl)azo]-1H-imidazolium halides, 1-methyl-4-[(methylphenylhydrazono)methyl]-pyridinium halides or alkyl sulfates.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylamino anthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes, mention may be made of the following compounds: Basic Blue 17, Basic Red 2.

Among the triarylmethane dyes that may be used according to the invention, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds: 2-β-hydroxyethlyamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N-(2'-chloro-4'-hydroxy)-phenylacetylamino-6-methoxy-1,4-benzoquinoneimine, 3-N(3'-chloro-4'-methyl-amino) phenylureido-6-methyl-1,4-benzoquinoneimine and 3-[4'-N-(ethylcarbamyl-methyl)amino]phenylureido-6-methyl-1, 4-benzoquinoneimine.

Among the dyes of tetraazapentamethine type that may be used according to the invention, mention may be made of the following compounds: 2-((E)-{(E)-[(1,3-dimethyl-1,3-dihydro-2H-imidazol-2-ylidene)hydrazono] methyl}diazenyl)-1,3-dimethyl-1H-imidazol-3-ium chloride; 2-{(E)-[(1Z)—N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2 (1H)-ylidene) hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)-pyridinium chloride; 1-(2-hydroxyethyl)-2-[(E)-((1E)-1-{(2E)-[1-(2-hydroxyethyl)-pyridin-2(1H)-ylidene]hydrazono}ethyl)diazenyl] pyridinium chloride; 1-methyl-2-((E)-{(E)-[(2Z)-(1-methyl-pyridin-2(1H)-ylidene)hydrazono]methyl}diazenyl)-pyridinium chloride; 1-(2-hydroxyethyl)-2-[(E)-((E)-{(2E)-[1-(2-hydroxyethyl)-pyridin-2(1H)-ylidene]hydrazono} methyl)diazenyl]pyridinium acetate.

Among the additional natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and especially henna-based poultices or extracts.

When they are present, the content of additional direct dyes in the composition generally ranges from 0.001% to 20% and preferably from 0.01% to 10% by weight relative to the weight of the composition.

The medium that is suitable for dyeing, also known as the dye support, generally comprises water or a mixture of water and of at least one organic solvent to dissolve the compounds that are not sufficiently water-soluble.

More particularly, the organic solvents are chosen from linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

The dye composition that is useful in the context of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

These above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dye composition that is useful in the context of the invention are not, or are not substantially, adversely affected by the envisaged addition(s).

The pH of the dye composition that is useful in the context of the invention is generally between 3 and 12 approximately and preferably between 5 and 11 approximately. It may be adjusted to the desired value by means of acidifying or basifying agents usually used in the dyeing of keratin fibres, or alternatively using standard buffer systems. Modifying the pH within these ranges will promote the formation of compound (I) or (II).

Among the acidifying agents, examples that may be mentioned include mineral acids, for instance hydrochloric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

Mention may be made, among the basifying agents, by way of example, of aqueous ammonia, alkaline carbonates, alkanolamines, such as mono-, di- and triethanolamines, and derivatives thereof, sodium hydroxide, potassium hydroxide and the compounds of formula (IV) below:

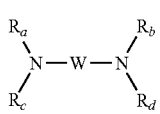
(IV)

in which W is a propylene residue optionally substituted with a hydroxyl group or a $C_1$-$C_4$ alkyl radical; and Ra, Rb, Rc and Rd, which may be identical or different, represent a hydrogen atom or a $C_1$-$C_4$ alkyl or $C_1$-$C_4$ hydroxyalkyl radical.

The oxidizing agent will also be necessary for obtaining simultaneous lightening of the keratin fibres (lightening dyeing) and/or when the composition contains oxidation bases or couplers.

The composition according to the invention may also contain one or more oxidizing agents.

The oxidizing agent may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The oxidizing agent will preferably be hydrogen peroxide.

In the case where the oxidizing agent(s) are present in the dye composition according to the invention, their amount will preferably range from 5% to 100% by weight and better still from 50% to 100% by weight relative to the total weight of the composition.

The dye composition that is useful in the context of the invention may be in various forms, such as in the form of liquids, creams or gels, or in any other form that is suitable for dyeing keratin fibres, and especially human hair.

A subject of the present invention is also the use of the compounds according to the invention, chosen from the compounds of formulae (I) and (II) as defined previously, and also the leuco forms, optical isomers, geometrical isomers and tautomers thereof, and the addition salts thereof with an acid or a base and the solvates thereof, for dyeing keratin fibres, in particular human keratin fibres such as the hair.

The dyeing process of the invention comprises the application to the keratin fibres of at least one dye composition as defined above.

When an oxidizing agent is used, it may be present in the composition of the invention. It may also be applied separately, as a pretreatment or post-treatment.

The application of the composition of the invention may optionally be followed by rinsing.

The leave-on time for the dye composition is generally between 3 and 60 minutes, preferably between 5 and 40 minutes and even more preferentially between 10 and 30 minutes.

The application temperature generally used is room temperature, preferably between 25 and 55° C.

A subject of the present invention is also a multi-compartment device or kit for performing the process for dyeing keratin fibres, described above.

The examples that follow serve to illustrate the invention without, however, being limiting in nature.

EXAMPLES

Example 1

Synthesis of the Dye Having the Following Formula

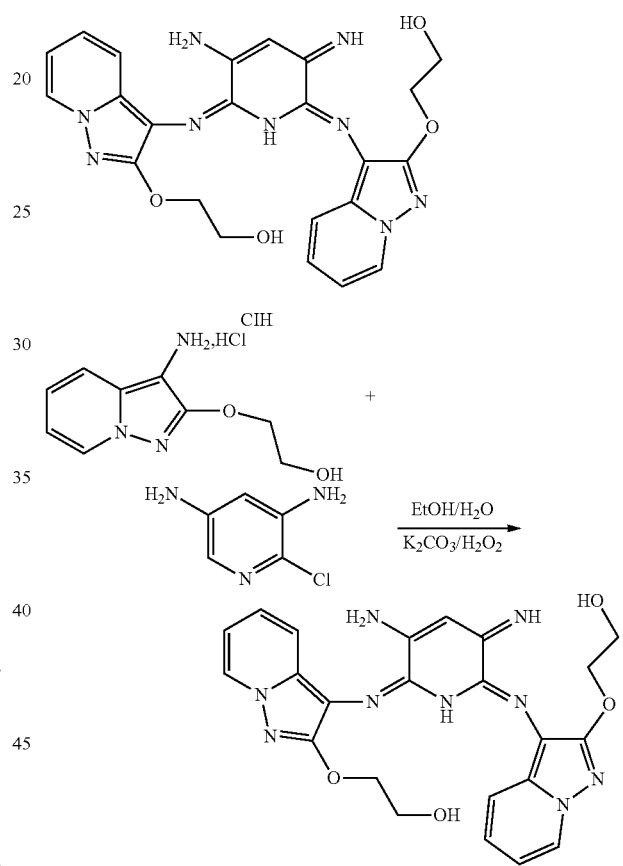

500 ml of ethanol are placed in a 1-litre one-necked round-bottomed flask equipped with a calcium chloride guard tube, followed by addition, with stirring, of g (0.2177 mol) of 2-[(3-aminopyrazolo[1,5-a]pyridin-2-yl)oxy]ethanol hydrochloride.

14.2 g (0.986 mol) of 2-chloropyridine-3,5-diamine and 60.3 ml (0.346 mol) of N-ethyl-N-(propan-2-yl)propan-2-amine are added to this solution.

The solution thus obtained is stirred at room temperature for 4 days. The black precipitate formed is isolated by filtration, washed with water and dried in a desiccator under vacuum at 30° C. in the presence of a desiccant, to constant weight. A black solid is thus obtained.

The spectrometric analyses show that the compound obtained corresponds to the above structure.

Example 2

Synthesis of 3,3-[(5-amino-3-iminopyridine-2,6-(1H,3H)-diylidene)-bis(nitrilopyrazolo[1,5-a]pyridine-3,2-diyloxy)]dipropan-1-ol hydrochloride

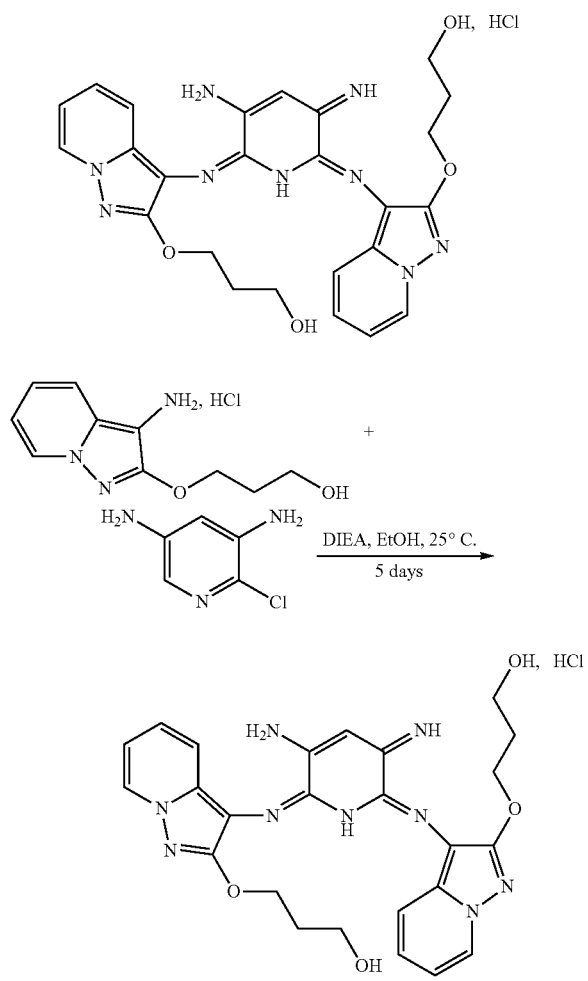

150 ml of ethanol are placed in a 500-ml one-necked round-bottomed flask equipped with a calcium chloride guard tube, followed by addition, with stirring, of 10.4 g (0.04268 mol) of 3-[(3-aminopyrazolo[1,5-a]pyridin-2-yl)oxy]propan-1-ol hydrochloride.

2.78 g (0.01940 mol) of 2-chloropyridine-3,5-diamine and 11.8 ml (0.06790 mol) of N-ethyl-N-(propan-2-yl)propan-2-amine are added to this solution.

The solution thus obtained is then stirred at room temperature for 4 days. The black precipitate formed is isolated by filtration, washed with water and dried in a desiccator under vacuum at 30° C. in the presence of a desiccant, to constant weight. A solid in the form of a black powder is thus obtained.

The spectrometric analyses show that the compound obtained corresponds to 3,3'-[(5-amino-3-iminopyridine-2,6-(1H,3H)-diylidene)bis(nitrilopyrazolo[1,5-a]-pyridine-3,2-diyloxy)]dipropan-1-ol hydrochloride

Example 3

Synthesis of N,N'-(5-amino-3-iminopyridine-2,6-(1H,3H)-diylidene)-bis{2-[2-(dimethylamino)ethoxy]pyrazolo[1,5-a]pyridin-3-amine}dihydrochloride

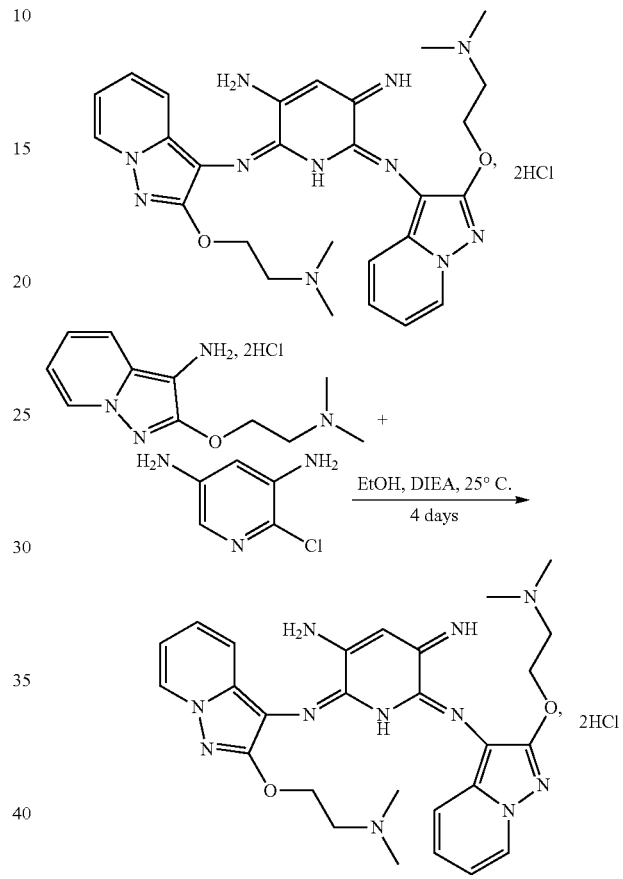

550 ml of ethanol are placed in a 1-litre one-necked round-bottomed flask equipped with a calcium chloride guard tube, followed by addition, with stirring, of 55 g (0.1876 mol) of 2-[2-(dimethylamino)ethoxy]pyrazolo[1,5-a]pyridin-3-amine dihydrochloride.

12.24 g (0.085 mol) of 2-chloropyridine-3,5-diamine and 52 ml (0.346 mol) of N-ethyl-N-(propan-2-yl)propan-2-amine are added to this solution.

The solution thus obtained is stirred at room temperature for 4 days. The viscous black oil obtained after removal of the solvent by evaporation under vacuum is chromatographed on a column of silica in normal phase with an eluent consisting of 50% dichloromethane and 50% methanol.

After removal of the solvent by evaporation under vacuum, the viscous black oil crystallizes in the form of a black solid.

The black solid formed is isolated by filtration, washed with water and then dried in a desiccator under vacuum at 30° C. in the presence of a desiccant, to constant weight.

The spectrometric analyses show that the compound obtained corresponds to N,N'-(5-amino-3-iminopyridine-2,6-(1H,3H)-diylidene)bis {2-[2-(dimethylamino)ethoxy]pyrazolo[1,5-a]pyridin-3-amine}dihydrochloride.

Example 4

Synthesis of N,N'-(5-amino-3-iminopyridine-2,6-(1H,3H)-diylidene)bis[2-(propan-2-yloxy)pyrazolo[1,5-a]pyridin-3-amine]hydrochloride

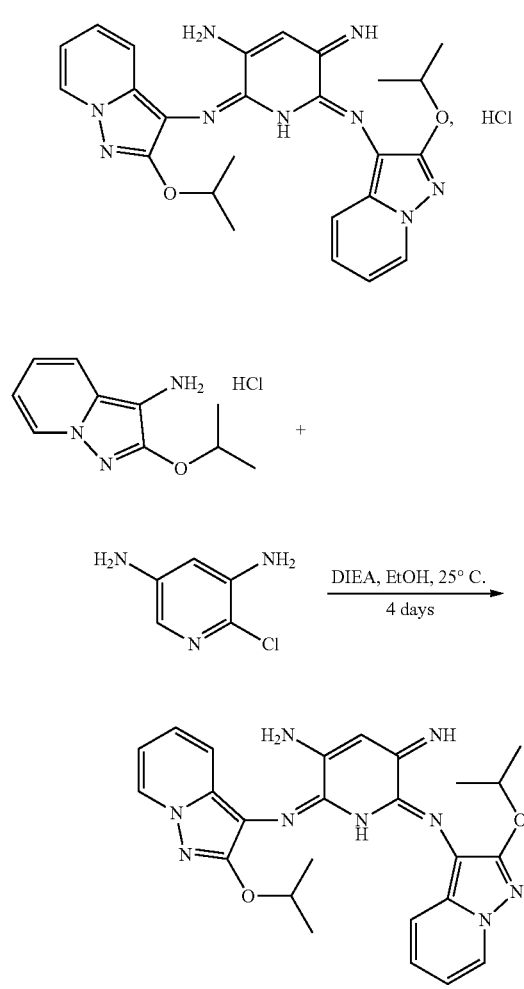

Example 5

Synthesis of N,N'-(5-amino-3-iminopyridine-2,6-(1H,3H)-diylidene)-bis{2-(propan-2-yloxy)ethoxy]pyrazolo[1,5-a]pyridin-3-amine}hydrochloride

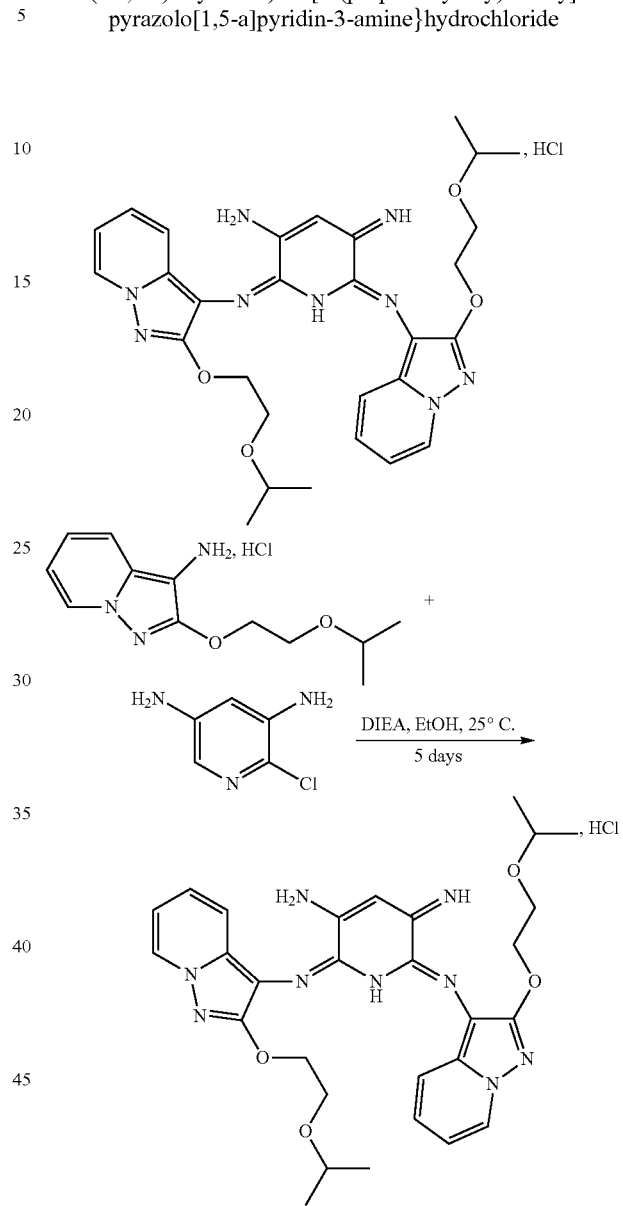

80 ml of ethanol are placed in a 250-ml one-necked round-bottomed flask equipped with a calcium chloride guard tube, followed by addition, with stirring, of 4.11 g (18.1 mmol) of 2-(propan-2-yloxy)pyrazolo[1,5-a]pyridin-3-amine hydrochloride.

1.18 g (8.21 mmol) of 2-chloropyridine-3,5-diamine and 5.0 ml (29 mol) of N-ethyl-N-(propan-2-yl)propan-2-amine are added to this solution.

The solution is then stirred at room temperature for 4 days. The black precipitate formed is isolated by filtration, washed with water and dried in a desiccator under vacuum at 30° C. in the presence of a desiccant, to constant weight. The compound is thus obtained in the form of a black powder.

The spectrometric analyses show that the compound obtained corresponds to N,N'-(5-amino-3-iminopyridine-2,6-(1H,3H)-diylidene)bis[2-(propan-2-yloxy)pyrazolo[1,5-a]pyridin-3-amine]hydrochloride.

150 ml of ethanol are placed in a 500-ml one-necked round-bottomed flask equipped with a calcium chloride guard tube, followed by addition, with stirring, of 11 g (48.5 mmol) of 2-[2-(propan-2-yloxy)ethoxy]pyrazolo[1,5-a]pyridin-3-amine hydrochloride.

2.64 g (18.4 mmol) of 2-chloropyridine-3,5-diamine and 11.2 ml (64.4 mmol) of N-ethyl-N-(propan-2-yl)propan-2-amine are added to this solution.

The solution is then stirred at room temperature for 4 days. The black precipitate formed is isolated by filtration, washed with water and dried in a desiccator under vacuum at 30° C. in the presence of a desiccant, to constant weight. The compound is thus obtained in the form of a black powder.

The spectrometric analyses show that the compound obtained corresponds to N,N'-(5-amino-3-iminopyridine-2, 6-(1H,3H)-diylidene)bis {2-[2-(propan-2-yloxy)ethoxy]pyrazolo[1,5-a]pyridin-3-amine}hydrochloride.

Example 6

Synthesis of N,N'-(5-amino-3-iminopyridine-2,6-(1H,3H)-diylidene)-bis{2-[2-(2-ethoxyethoxy)ethoxy]pyrazolo[1,5-a]pyridin-3-amine}hydrochloride

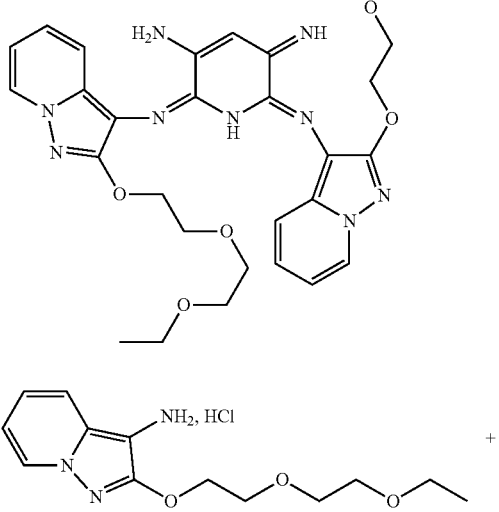

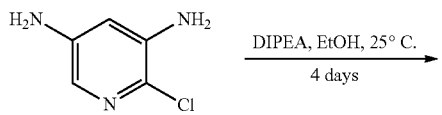

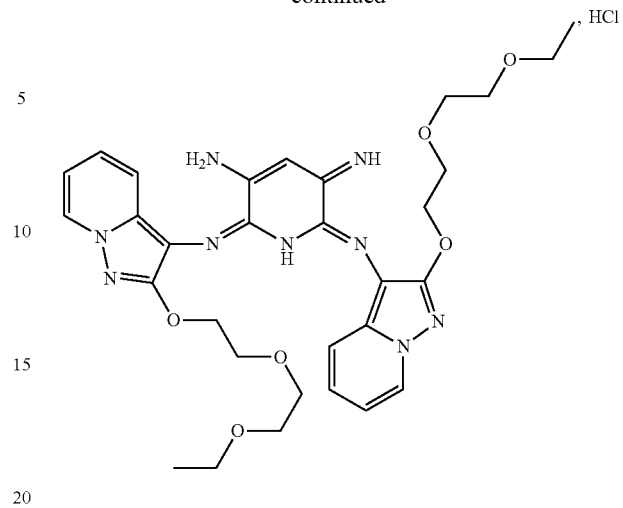

150 ml of ethanol are placed in a 500-ml one-necked round-bottomed flask equipped with a calcium chloride guard tube, followed by addition, with stirring, of 10.0 g (33.14 mmol) of 2-[2-(2-ethoxyethoxy)ethoxy]pyrazolo[1,5-a]pyridin-3-amine hydrochloride.

2.16 g (15.06 mmol) of 2-chloropyridine-3,5-diamine and 9.2 ml (52.71 mmol) of N-ethyl-N-(propan-2-yl)propan-2-amine are added to this solution.

The solution is then stirred at room temperature for 4 days. The black precipitate formed is isolated by filtration, washed with water and dried in a desiccator under vacuum at 30° C. in the presence of a desiccant, to constant weight. The compound is obtained in the form of a black powder.

The spectrometric analyses show that the compound obtained corresponds to N,N'-(5-amino-3-iminopyridine-2,6-(1H,3H)-diylidene)bis {2-[2-(2-ethoxyethoxy)ethoxy]pyrazolo[1,5-a]pyridin-3-amine}hydrochloride.

Example 7

Examples of Dyeing at Neutral pH

The following dye compositions are prepared from the ingredients indicated in the table below:

| | |
|---|---|
| Dye[1] | $10^{-3}$ mol |
| pH 7 dye support | [2] |
| Demineralized water qs | 100 g |

[1] Dye synthesized in one of Examples 1 to 6 above:

Dye 1 (synthesized in Example 1)

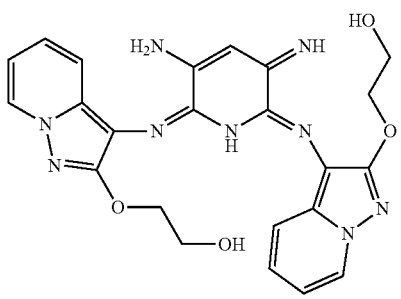 [SMILES: N=C1C=C(N)/C(=N\c2c(OCCO)nn3ccccc23)N/C1=N\c1c(OCCO)nn2ccccc12]

-continued
Dye 2 (synthesized in Example 2)
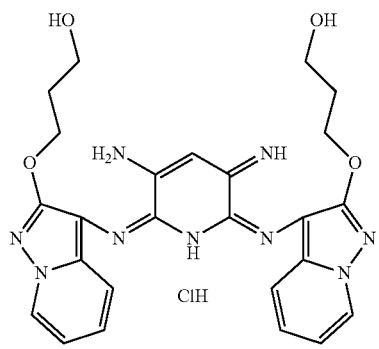 [SMILES: N=C1C=C(N)/C(=N\c2c(OCCCO)nn3ccccc23)N/C1=N/c1c(OCCCO)nn2ccccc12 ; Cl]
Dye 3 (synthesized in Example 3)
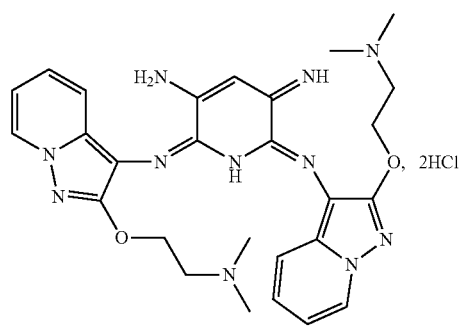 [SMILES: CN(C)CCOc1nn2ccccc2c1/N=C1\N/C(=N/c2c(OCCN(C)C)nn3ccccc23)C(N)=CC1=N ; "2HCl"]
Dye 4 (synthesized in Example 4)
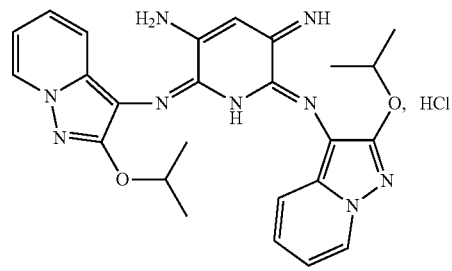 [SMILES: CC(C)Oc1nn2ccccc2c1/N=C1\N/C(=N/c2c(OC(C)C)nn3ccccc23)C(N)=CC1=N ; Cl]
Dye 5 (synthesized in Example 5)
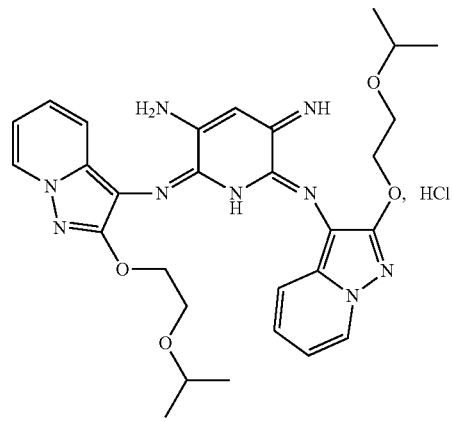 [SMILES: CC(C)OCCOc1nn2ccccc2c1/N=C1\N/C(=N/c2c(OCCOC(C)C)nn3ccccc23)C(N)=CC1=N ; Cl]

Dye 6 (synthesized in Example 6)

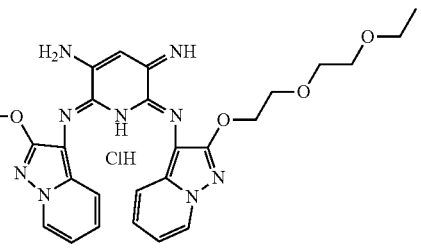

| (2) pH 7 dye support | |
|---|---|
| 96° ethyl alcohol | 20.8 g |
| Pentasodium salt of diethylenetriaminepentaacetic acid as an aqueous 40% solution | 0.48 g AM* |
| C$_8$-C$_{10}$ alkyl polyglucoside as an aqueous 60% solution | 3.6 g AM* |
| Benzyl alcohol | 2.0 g |
| Polyethylene glycol containing 8 ethylene oxide units | 3.0 g |
| Na$_2$HPO$_4$ | 0.28 g |
| KH$_2$PO$_4$ | 0.46 g |

* AM: Active material

Each mixture obtained was applied to locks of grey hair containing 90% white hairs. After a leave-on time of 30 minutes, the locks are rinsed, washed with a standard shampoo, rinsed again and then dried.

The shades obtained are given in the table below:

| | Dye | | | | | |
|---|---|---|---|---|---|---|
| | 1 | 2 | 3 | 4 | 5 | 6 |
| Shade observed | Grey neutral | Grey dark neutral | Grey dark | Grey | Grey light | Grey light |

For the colourings in the presence of an oxidizing agent: at the time of use, each of the compositions described above was mixed with an equal weight of 20-volumes aqueous hydrogen peroxide solution (6% by weight relative to the total weight of 100 grams). A final pH of 7 is obtained.

The shades obtained are given in the table below:

| | Dye | | | | | |
|---|---|---|---|---|---|---|
| | 1 | 2 | 3 | 4 | 5 | 6 |
| Shade observed | Grey neutral | Grey | Grey | Grey | Grey | Grey |

Example 8

Examples of Dyeing in Basic Medium

The following dye compositions are prepared:

| Dye 1, 2, 3, 4, 5 or 6 | 10$^{-3}$ mol |
|---|---|
| pH 9.5 dye support | (3) |
| Demineralized water qs | 100 g |

(3): pH 9.5 dye support

| 96° ethyl alcohol | 20.8 g |
|---|---|
| Pentasodium salt of diethylenetriaminepentaacetic acid as an aqueous 40% solution | 0.48 g AM* |

-continued

| C$_8$-C$_{10}$ alkyl polyglucoside as an aqueous 60% solution | 3.6 g AM* |
|---|---|
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 g |

*AM: Active material

Each mixture obtained was applied to locks of grey hair containing 90% white hairs. After a leave-on time of 30 minutes, the locks are rinsed, washed with a standard shampoo, rinsed again and then dried.

The shades obtained are given in the table below:

| | Dye | | | | | |
|---|---|---|---|---|---|---|
| | 1 | 2 | 3 | 4 | 5 | 6 |
| Shade observed | Grey | Grey neutral | Grey dark | Grey | Grey | Grey |

For the colourings in the presence of an oxidizing agent: at the time of use, each of the compositions described above was mixed with an equal weight of 20-volumes aqueous hydrogen peroxide solution. A final pH of 9.5 is obtained.

The shades obtained are given in the table below:

| Dye | 1 | 2 | 3 | 4 | 5 | 6 |
|---|---|---|---|---|---|---|
| Shade observed | Grey | Grey neutral | Grey dark | Grey | Grey | Grey |

The colours of the locks thus obtained with dyes 1 to 6 and also with compound 35 used in the same pH 9.5 dye support as that described above, and in the presence of an oxidizing agent, were evaluated in the CIE L* a* b* system, using a Minolta Spectrophotometer CM2600D colorimeter (specular components included, illuminant D65, angle 10°).

In this L* a* b* system, the three parameters denote, respectively, L*: the colour intensity, a*: the green/red colour axis, and b*: the blue/yellow colour axis. For the intensity, the lower the value, the darker and more intense the colour.

The variation in colouring or gain in colour build-up is the difference in colour between the locks of natural grey hair (NG) treated with the composition according to the invention, and the untreated locks, and is measured by ($\Delta E$) according to the following equation:

$$\Delta E = \sqrt{(L^*-L_o^*)^2 + (a^*-a_o^*)^2 + (b^*-b_o^*)^2}$$

In this equation, $L^*$, $a^*$ and $b^*$ represent the values measured on NG dyed hair according to the invention, and $L_o^*$, $a_o^*$ and $b_o^*$ represent the values measured on the untreated locks.

The higher the value of $\Delta E$, the greater the gain in colour build-up.

The results are given in the table below:

| Dye | L | a | b | $\Delta E$ |
|---|---|---|---|---|
| 1 | 24.54 | 0.41 | 1.36 | 37.98 |
| 2 | 22.21 | 0.26 | 1.05 | 40.25 |
| 3 | 25.78 | −0.39 | 1.8 | 36.69 |
| 4 | 21.74 | −0.31 | 1.27 | 40.63 |
| 5 | 23.67 | 1.96 | 3.85 | 37.91 |
| 6 | 25.06 | 0.54 | 1.59 | 37.4 |
| Compound 35 | 25.64 | 1.36 | 3.2 | 36.27 |

The invention claimed is:

1. A compound chosen from dyes of azomethine type comprising two pyrazolopyridine units, chosen from compounds of formulae (I) or (II) and leuco forms thereof, optical or geometrical isomers thereof, tautomers thereof, addition salts thereof with an acid or a base, and solvates or hydrates thereof:

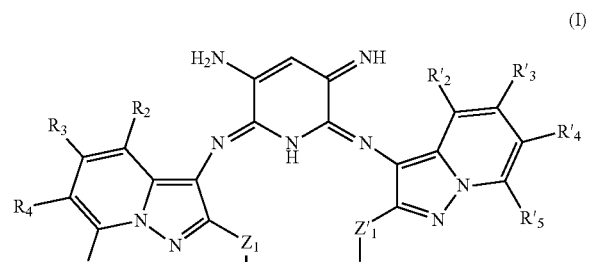

(I)

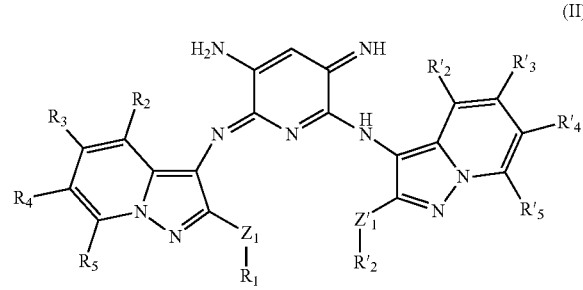

(II)

wherein in formulae (I) and (II):
Z$_1$ represents an oxygen atom or a group —N(R$_6$)—;
Z'$_1$ represents an oxygen atom or a group —N(R'$_6$)—;
with the proviso that when Z$_1$ represents —N(R$_6$)— and/or Z'$_1$ represents —N(R'$_6$)—, then R$_1$ and R$_6$ and/or R'$_1$ and R'$_6$, respectively, may form, together with the nitrogen atom to which they are attached, an optionally substituted, 5- to 8-membered, optionally cationic, saturated, unsaturated or aromatic heterocycle;

R$_1$, R'$_1$, R$_6$, and R'$_6$ each independently represent:
a hydrogen atom,
a C$_1$-C$_{10}$ alkyl radical optionally interrupted with one or more non-adjacent heteroatoms and/or optionally substituted, optionally with one or more groups chosen from i) hydroxyl, ii) optionally substituted, 5- to 8-membered, cationic or non-cationic, saturated, unsaturated or aromatic (hetero)cycle, iii) —N(R') R'', and iv) —N$^+$R'R''R''', with R', R'' and R''' each independently representing a C$_1$-C$_6$ alkyl group; or
an optionally substituted, 5- to 8-membered, cationic or non-cationic, saturated, unsaturated or aromatic (hetero)cyclic radical;

R$_2$, R$_3$, R$_4$, R$_5$, R'$_2$, R'$_3$, R'$_4$ and R'$_5$ each independently represent:
a hydrogen atom,
an optionally substituted C$_1$-C$_4$ alkyl radical, or
a group chosen from —NH$_2$, —N(H)R$_{10}$, —N(R$_{11}$)R$_{12}$, OH or —OR$_9$, with R$_9$ and R$_{10}$ representing an optionally substituted, linear or branched C$_1$-C$_6$ alkyl, R$_{11}$ and R$_{12}$, which may be identical or different, representing an optionally substituted, linear or branched C$_1$-C$_6$ alkyl, or R$_{11}$ and R$_{12}$ forming, together with the nitrogen atom to which they are attached, a saturated, unsaturated or aromatic 5- to 8-membered heterocycle optionally containing one or more other heteroatoms or groups chosen from N, O, S, S(O)$_2$ and C(O), the heterocycle being optionally substituted; or
R$_2$, R$_3$, R$_4$, R$_5$, R'$_2$, R'$_3$, R'$_4$ and R'$_5$ may form, in pairs with adjacent radicals, an optionally substituted, saturated or unsaturated (hetero)cycle;
it being understood that when the compound of formula (I) or (II) is positively charged, then it comprises as many anionic counterions as cationic charges to achieve the electrical neutrality of the molecule.

2. The compound according to claim 1, wherein R$_1$ and R'$_1$ are chosen from: i) C$_1$-C$_6$ alkyl; ii) C$_1$-C$_{10}$ alkyl substituted with one or more hydroxyl groups; iii) C$_1$-C$_6$ alkyl substituted with one or more amino or (di)(C$_1$-C$_4$)alkylamino groups; iv) C$_1$-C$_6$ alkyl substituted with a nitrogenous heterocycle; or v) —[(CH$_2$)$_m$—O]$_p$-L-Y, with p =1, 2 or 3, m =1, 2 or 3, L denoting a linear or branched, saturated C$_1$-C$_6$ divalent hydrocarbon-based group, and Y denoting a hydroxyl group or a hydrogen atom.

3. The compound according to claim 1, wherein R$_2$, R'$_2$, R$_3$, R'$_3$, R$_4$, R'$_4$, R$_5$ and R'$_5$ independently represent a hydrogen atom or a C$_1$-C$_4$ alkyl radical, or R$_4$ and R$_5$ and R'$_4$ and R'$_5$ together form a 5- to 8-membered ring.

4. The compound according to claim 1, chosen from those of formula (I') or (II'):

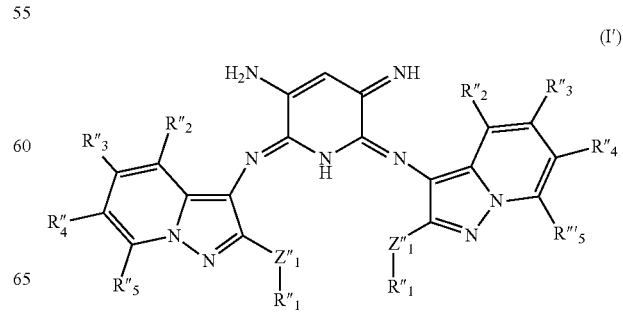

(I')

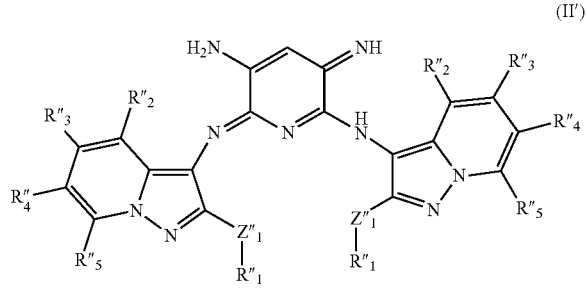

wherein in formulae (I') and (II'):
- $Z''_1$ is chosen from an oxygen atom and a group —N($R''_6$)—; and when $Z''_1$ represents —N($R''_6$)—, then $R''_1$ and $R''_6$ may form, together with the nitrogen atom to which they are attached, an optionally substituted, 5- or 6-membered, saturated, unsaturated or aromatic heterocycle;
- $R''_1$ represents a $C_1$-$C_6$ alkyl radical, optionally interrupted with one or more non-adjacent oxygen atoms, and/or optionally substituted with:
  - a hydroxyl radical,
  - a di($C_1$-$C_4$)alkylamino radical, or
  - a heterocycle optionally substituted with one or more $C_1$-$C_4$ alkyl and/or hydroxyl radicals and chosen from pyrrolidine, piperidine, morpholine, piperazine and imidazole;
- $R''_6$ represents:
  - a hydrogen atom; or
  - a $C_1$-$C_{10}$ alkyl radical optionally substituted with a hydroxyl radical;
- $R''_2$, $R''_3$, $R''_4$ and $R''_5$ each independently represent:
  - a hydrogen atom; or
  - a $C_1$-$C_4$ alkyl radical;

and the leuco forms thereof, isomers or tautomers thereof, and also the addition salts thereof with an acid or a base and the solvates or hydrates thereof.

5. The compound according to claim 4, wherein $Z''_1$ represents an oxygen atom; and $R''_1$ denotes a linear or branched $C_1$-$C_6$ alkyl radical, a $C_1$-$C_6$ hydroxyalkyl radical, a di($C_1$-$C_4$ alkyl)amino($C_1$-$C_6$ alkyl) radical, a radical —[(CH$_2$)$_{m'}$—O]$_{p'}$-L'-Y' with p'=1, 2, or 3, m'=2 or 3, L' denoting a saturated linear $C_1$-$C_6$ divalent hydrocarbon-based radical, and Y' denoting a hydroxyl radical or a hydrogen atom, or an alkyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals.

6. The compound according to claim 4, wherein $Z''_1$ represents NH; $R''_1$ denotes a $C_1$-$C_6$ hydroxyalkyl radical, a di($C_1$-$C_4$ alkyl)amino($C_1$-$C_6$ alkyl) radical, or an alkyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals or hydroxyl.

7. The compound according to claim 4, wherein $Z''_1$ represents —N($R''_6$)—; and $R''_1$ and $R''_6$ each independently denote a $C_1$-$C_6$ alkyl radical or a $C_1$-$C_6$ hydroxyalkyl radical; or $R''_1$ forms with $R''_6$ a ring, this ring being chosen from pyrrolidinyl, piperidyl, morpholinyl and piperazinyl rings optionally substituted with one or more $C_1$-$C_4$ alkyl and/or hydroxyl radicals.

8. A composition for dyeing keratin fibers comprising, in a medium that is suitable for dyeing keratin fibers, at least one compound according to claim 1.

9. The composition according to claim 8, wherein the compound is present in an amount ranging from 0.01% to 15% by weight, relative to the total weight of the composition.

10. The composition according to claim 8, further comprising one or more oxidizing agents.

11. A process for dyeing keratin fibers, comprising applying a dye composition according to claim 8 to the fibers.

12. A process for preparing compounds of formulae (I) and according to claim 1, where formulae (I) and (II) are symmetrical:

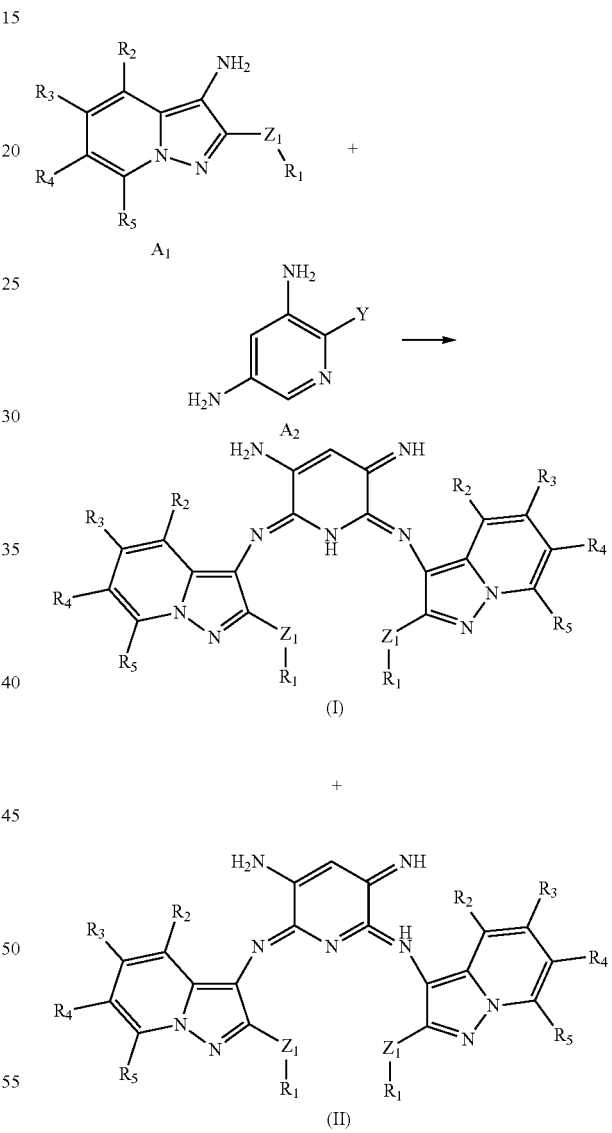

comprising:
a) in a first stage, reacting at least two molar equivalents of pyrazolo[1,5-a]pyridine compound $A_1$ comprising an amino group in position 3 with a pyridine compound $A_2$ which is free in position 6 and comprising in position 2 either a hydrogen atom or an electrofugal group,
optionally performed i) in a polar protic solvent chosen from water or a mixture of water/$C_1$-$C_{10}$ alcohol, ii)

and/or in the presence of one or more mineral or organic basifying agents, iii) and/or in the presence of a chemical oxidizing agent, iv) and/or at a temperature ranging from 25° C. to the reflux temperature of the solvent; and b) in a second stage, maintaining the reaction medium under stirring for a time ranging from 5 minutes to 48 hours;

c) wherein the reaction products (I) and (II) are optionally purified;

it being understood that, in formulae $A_1$, $A_2$, (I) and (II), the radicals $R_1$ to $R_5$ and $Z_1$ are as defined in claim 1, and Y represents a hydrogen atom or an electrofugal group selected from halogen, (poly)halo($C_1$-$C_6$ alkoxy), or (poly)(halo)($C_1$-$C_6$ alkyl)—$SO_3$—.

13. A process for preparing compounds of formulae (I) and (II) according to claim 1, where formulae (I) and (II) are symmetrical or dissymmetrical:

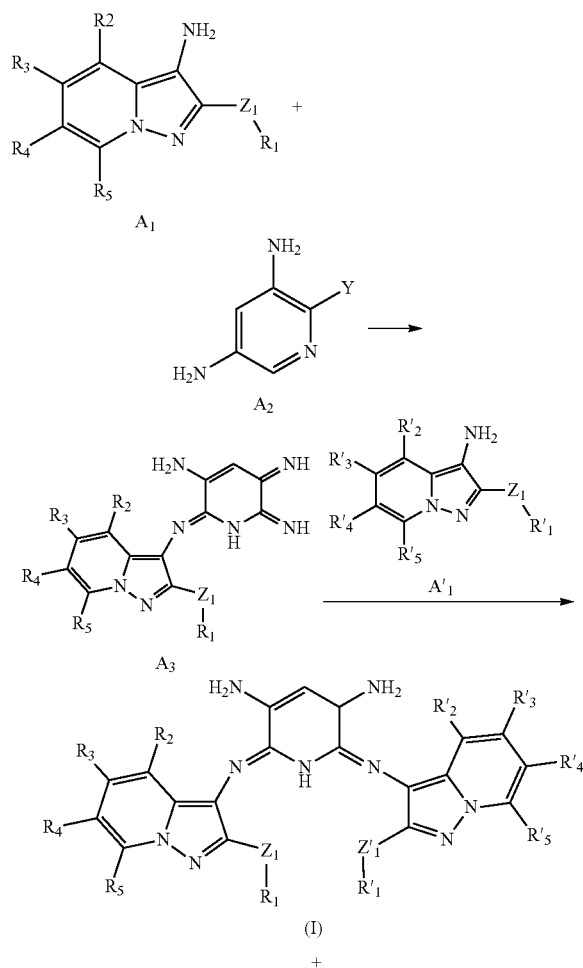

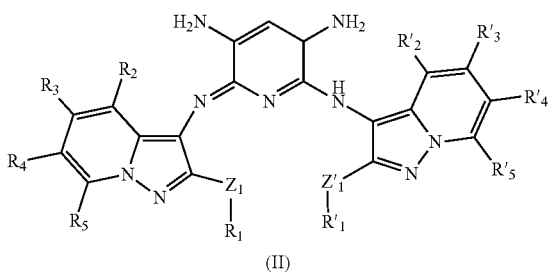

comprising:

a) in a first stage, reacting one molar equivalent of pyrazolo[1,5-a]pyridine compound $A_1$ comprising an amino group in position 3 with a pyridine compound $A_2$ which is free in position 6 and comprising in position 2 either a hydrogen atom or an electrofugal group, optionally performed i) in a polar protic solvent chosen from water or a mixture of water/$C_1$-$C_{10}$ alcohol, ii) and/or in the presence of one or more mineral or organic basifying agents, iii) and/or in the presence of a chemical oxidizing agent, iv) and/or at a temperature ranging from 25° C. to the reflux temperature of the solvent; and b) in a second stage, maintaining the reaction medium under stirring for a time of between 5 minutes and 48 hours;

c) wherein a reaction product $A_3$ is then optionally purified;

d) wherein if compound $A_3$ is then purified, compound $A_3$ once purified reacts with a molar equivalent of pyrazolo[1,5-a]pyridine compound $A'_1$ comprising an amino group in position 3, under the same conditions as steps a) and b), to give the products (I) and (II), which are then optionally purified;

e) wherein if compound $A_3$ is not then purified, compound $A_3$ reacts with a molar equivalent of pyrazolo[1,5-a]pyridine compound $A'_1$ comprising an amino group in position 3, under the same conditions as steps a) and b), to give the products (I) and (II), which are optionally purified;

it being understood that, in formulae $A_1$, $A_2$, $A_3$, (I) and (II), the radicals $R_1$ to $R_5$, $Z_1$, $R'_1$ to $R'_5$, Y and $Z'_1$ are as defined previously.

14. A compound of formula $A_3$ as defined in claim 13, the optical isomers thereof, geometrical isomers thereof and the tautomers thereof, and also the addition salts thereof with an acid or a base, and the solvates thereof.

* * * * *